(12) United States Patent
Mei et al.

(10) Patent No.: US 11,987,736 B2
(45) Date of Patent: May 21, 2024

(54) QUANTUM DOT LIGAND, QUANTUM DOT MATERIAL AND QUANTUM DOT LIGHT EMITTING DEVICE

(71) Applicant: BOE TECHNOLOGY GROUP CO., LTD., Beijing (CN)

(72) Inventors: Wenhai Mei, Beijing (CN); Zhenqi Zhang, Beijing (CN); Xiaoyuan Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 967 days.

(21) Appl. No.: 16/965,457

(22) PCT Filed: Sep. 17, 2019

(86) PCT No.: PCT/CN2019/106235
§ 371 (c)(1),
(2) Date: Jul. 28, 2020

(87) PCT Pub. No.: WO2021/051279
PCT Pub. Date: Mar. 25, 2021

(65) Prior Publication Data
US 2023/0119074 A1    Apr. 20, 2023

(51) Int. Cl.
*C09K 11/02* (2006.01)
*B82Y 20/00* (2011.01)
(Continued)

(52) U.S. Cl.
CPC .......... *C09K 11/025* (2013.01); *C07C 211/54* (2013.01); *C09K 11/883* (2013.01);
(Continued)

(58) Field of Classification Search
CPC .. C09K 11/025; C09K 11/883; H10K 50/115; B82Y 20/00; B82Y 40/00
(Continued)

(56) References Cited

U.S. PATENT DOCUMENTS 6,090,552 A * 6/2000 Marder et al. ......... G11C 13/04
264/435
6,090,332 A 7/2000 Marder et al.
2010/0258789 A1 10/2010 Akai et al.

FOREIGN PATENT DOCUMENTS

CN 107267140 10/2017
CN 109233800 1/2019
(Continued)

OTHER PUBLICATIONS

Planells, M, Reynolds, et al. "Synthesis and optical characterisation of triphenylamine-based hole extractor materials for CdSe quantum dots" Physical chemistry chemical physics, vol. 15, No. 20, pp. 7679-7684.
(Continued)

Primary Examiner — Thinh T Nguyen
(74) Attorney, Agent, or Firm — Leason Ellis LLP

(57) ABSTRACT

Embodiments of the present disclosure provide a quantum dot ligand, a quantum dot material, and a quantum dot light emitting device. In a quantum dot ligand of general formula (I), n is 1, 2, 3, or 4; two of X, Y, and Z are G1 group and G2 group, respectively, and the remaining one is selected from the group consisting of G1 group, G2 group, and hydrogen, wherein the G1 group, for each occurrence, is independently selected from $-(CH_2)_m-L-(CH_2)_n-R^1$, wherein $R^1$ is a coordination group, m is 0 to 6, n is 0 to 6,
(Continued)

and L is a divalent group or absent; the G2 group, for each occurrence, is independently selected from a $C_{4-20}$ alkyl having a carbon chain with more than 4 carbon atoms.

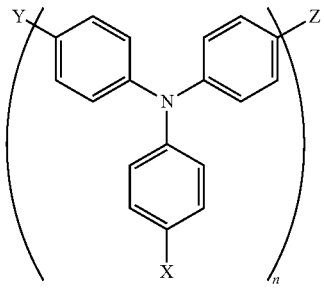

(I)

17 Claims, 6 Drawing Sheets

(51) Int. Cl.
*C07C 211/54* (2006.01)
*C09K 11/88* (2006.01)
*H10K 50/115* (2023.01)
*B82Y 40/00* (2011.01)

(52) U.S. Cl.
CPC ............ *H10K 50/115* (2023.02); *B82Y 20/00* (2013.01); *B82Y 40/00* (2013.01)

(58) Field of Classification Search
USPC .............................................. 257/13; 438/22
See application file for complete search history.

(56) References Cited

FOREIGN PATENT DOCUMENTS

JP 2008130654 A 6/2008
WO 2009/141288 A2 11/2009

OTHER PUBLICATIONS

Extended European Search Report in European Application No. 19945418.2, dated Aug. 8, 2022.
Rybakiewicz R, Zapala J, Djurado D, Nowakowski R, Toman P, Pfleger J, Verilhac JM, Zagorska M, Pron A. Naphthalene bisimides asymmetrically and symmetrically N-substituted with triarylamine-comparison of spectroscopic, electrochemical, electronic and self-assembly properties. Phys Chem Chem Phys. Feb. 2013;15(5) 1578-1587. doi:10.1039/c2cp43505e. PMID: 23243662.
Skorka, L., Mouesca, JM., Dubois, L., Szewczyk, E., Wielgus, I., Maurel, V., & Kulszewicz-Bajer, I. (2015). Formation of High-Spin States (S=3/2 and S=2) in Linear Oligo- and Polyarylamines. The journal of physical chemistry. B. 119.10.1021/acs.jpcb.5b08390.
Pron, A., Reghu, R.R., Rybakiewicz, R., Cybulski, H., Djurado, D., Gražulevičius, J.V., Zagorska, M., Kulszewicz-Bajer, I., & Verilhac, J.M. (2011). Triarylamine Substituted Arylene Bisimides as Solution Processable Organic Semiconductors for Field Effect Transistors. Effect of Substituent Position on Their Spectroscopic, Electrochemical, Structural, and Electrical Transport Properties. Journal of Physical Chemistry C, 115, 15008-15017.
Dobrzyńska, E., Jouni, M., Gawryś, P., Gambarelli, S., Mouesca, J. M., Djurado, D., Dubois, L., Wielgus, I., Maurel, V., & Kulszewicz-Bajer, I. (2012). Tuning of ferromagnetic spin interactions in polymeric aromatic amines via modification of their π-conjugated system. The journal of physical chemistry. B, 116(51), 14968-14978. https://doi.org/10.1021/jp309935a.
Chen, W., Wang, K., Liaw, D., Lee, K., & Lai, J. (2010). N,N, N', N'-Tetraphenyl-1,4-phenylenediamine-Fluorene Alternating Conjugated Polymer: Synthesis, Characterization, and Electrochromic Application. Macromolecules, 43, 2236-2243.
Bardecker, J.A., Ma, H., Kim, T., Huang, F., Liu, M., Cheng, Y., Ting, G.G., & Jen, A.K. (2008). Self-assembled Electroactive Phosphonic Acids on ITO: Maximizing Hole-Injection in Polymer Light-Emitting Diodes. Advanced Functional Materials, 18.

* cited by examiner

QUANTUM DOT LIGAND, QUANTUM DOT MATERIAL AND QUANTUM DOT LIGHT EMITTING DEVICE

CROSS-REFERENCE TO RELATED PATENT APPLICATIONS

This application is a U.S. National Stage Application under 35 U.S.C. § 371 of International Patent Application No. PCT/CN2019/106235, filed Sep. 17, 2019, which is incorporated by reference in its entirety.

TECHNICAL FIELD

Embodiments of the present disclosure relate to a quantum dot ligand, a quantum dot material, and a quantum dot light emitting device.

BACKGROUND

Quantum dots (QDs) are inorganic semiconductor nanoparticles that are synthesized by a solution method and have a size between 1 and 10 nm. The size is approximately or less than the exciton Bohr radius of the particles. Quantum dots tend to agglomerate due to their small size and large specific surface area, and there are many surface defects on quantum dots. Therefore, in use, the surface of the quantum dot is usually coated with an organic surface ligand, which not only plays a protective role but also makes the quantum dot have better solubility in a solution. The migration of carriers (electrons and holes) in quantum dots is restricted within the quantum dots, which affords quantum dots unique optical and electrical properties. Due to the unique size-dependence, the properties of light absorption and light emission of quantum dots can be easily adjusted by controlling the size, shape or surface structure of particles.

SUMMARY

At least one embodiment of the present disclosure provides a quantum dot ligand of general formula (I),

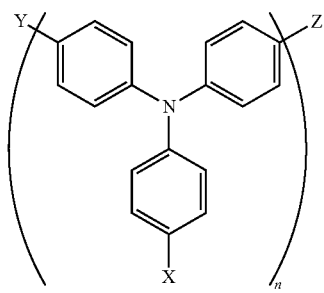

(I)

wherein n is 1, 2, 3 or 4; two of X, Y and Z are G1 and G2 groups respectively, and the remaining one is selected from the group consisting of G1 group, G2 group and hydrogen; wherein the G1 group, for each occurrence, is independently selected from $-(CH_2)_m$-L-$(CH_2)_n-R^1$, wherein $R^1$ is a coordination group, m is 0 to 6, n is 0 to 6, L is a divalent group or is absent; and the G2 group, for each occurrence, is independently selected from $C_{4-20}$ alkyl having a carbon chain with more than 4 carbon atoms.

For example, at least one embodiment of the present disclosure provides a quantum dot ligand having a molecular structure of:

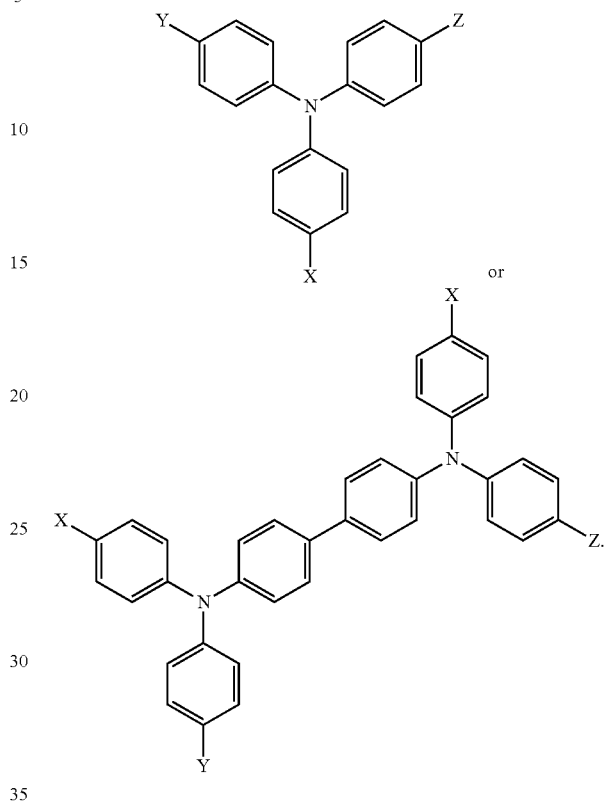

For example, in the quantum dot ligand provided by at least one embodiment of the present disclosure, G1 is $-(CH_2)_m$-L-$(CH_2)_n-R^1$, wherein L is absent or selected from the group consisting of O, NH, S, a linear $C_1$-$C_6$-alkylene, a branched $C_3$-$C_6$-alkylene, a $C_3$-$C_6$-cycloalkylene and a $C_6$-$C_{12}$ arylene, and L is optionally substituted with a substituent(s) selected from the group consisting of oxo, halogen, CN, mercapto, hydroxyl, $C_{1-6}$ alkyl, and $C_3$-$C_6$-cycloalkyl; $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group; m is an integer of 1 to 6; n is an integer of 0 to 6.

For example, in the quantum dot ligand provided by at least one embodiment of the present disclosure, G1 is -$CH_2$-L-$(CH_2)_2-R^1$, wherein $R^1$ is $NH_2$, and L is O, NH, S, or $CH_2$.

For example, in the quantum dot ligand provided by at least one embodiment of the present disclosure, G1 is $-R^1$, wherein $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

For example, in the quantum dot ligand provided by at least one embodiment of the present disclosure, the G2 group is a linear alkyl with 4 to 8 carbon atoms; or the G2 group is a branched alkyl with 6 to 12 carbon atoms in the main chain and 2 to 6 carbon atoms in the branch chain.

For example, at least one embodiment of the present disclosure provides a quantum dot ligand having a molecular structure of:

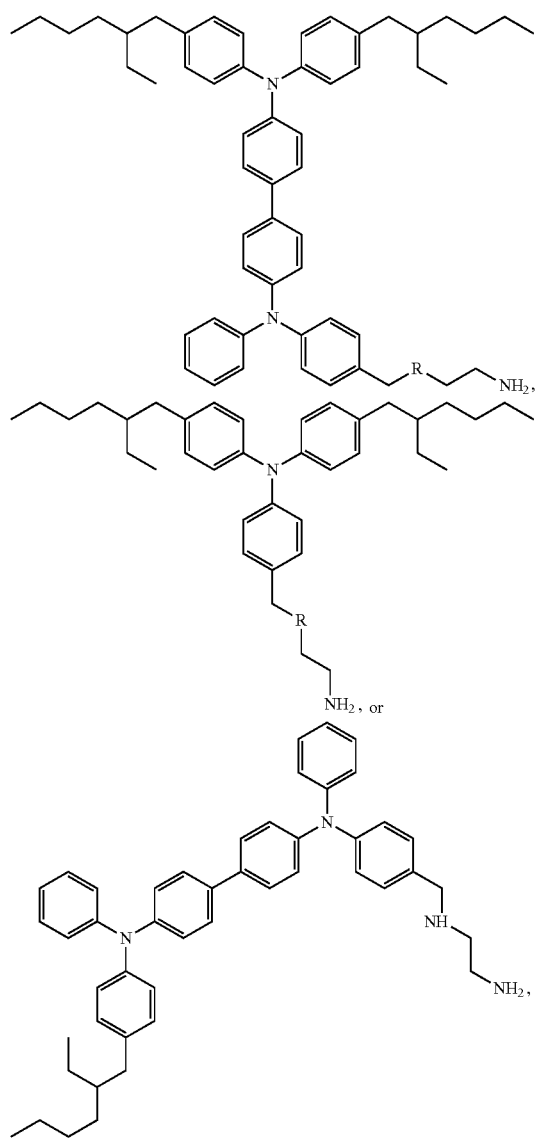

wherein R is O, NH, S or CH$_2$.

At least one embodiment of the present disclosure further provides a quantum dot material, which includes a quantum dot and the quantum dot ligand described in any one of the above embodiments.

For example, in the quantum dot material provided by at least one embodiment of the present disclosure, the quantum dot is selected from the group consisting of CdS, CdSe, CdTe, ZnSe, InP, PbS, CsPbCl$_3$, CsPbBr$_3$, CsPhI$_3$, CdS/ZnS, CdSe/ZnS, ZnSe, InP/ZnS, PbS/ZnS, CsPbCl$_3$/ZnS, CsPbBr$_3$/ZnS and CsPhI$_3$/ZnS.

At least one embodiment of the present disclosure further provides a quantum dot light emitting device including a quantum dot light emitting layer, wherein the quantum dot light emitting layer comprises the quantum dot material described in any one of the above embodiments.

For example, the quantum dot light emitting device provided by at least one embodiment of the present disclosure further includes: a hole injection layer, a hole transport layer, an electron injection layer, and an electron transport layer.

BRIEF DESCRIPTION OF THE DRAWINGS

In order to more clearly explain the technical solutions of the embodiments disclosed herein, the drawings of the embodiments will be briefly described below. Obviously, the drawings in the following description only relate to some embodiments disclosed herein, rather than limit the present invention.

DETAILED DESCRIPTION

To make the objectives, technical solutions, and advantages of embodiments disclosed herein more clear, the technical solutions of the embodiments disclosed herein will be described clearly and completely in conjunction with the drawings of the embodiments disclosed herein. Obviously, the described embodiments are a part of embodiments of the present invention, but not all the embodiments. Based on the described embodiments of the present invention, all other embodiments obtained by a person of ordinary skill in the art without creative labor should fall within the protection scope of the present invention.

Unless otherwise defined, the technical or scientific terms used in the present disclosure shall have the usual meanings understood by persons of ordinary skill in the field to which the invention belongs. The word "including", "comprising" or other similar words used in this disclosure means that the elements or objects appearing before the word cover the elements or objects listed after the word and their equivalents, but do not exclude other elements or objects.

The surface of quantum dots is usually coated with a layer of organic ligands. These surface ligands not only determine the solubility and the surface chemical functionality of quantum dots, but also greatly affect the fluorescence quantum yield and electrical properties of quantum dots. In order to make quantum dots dissolve stably in a solution, a long-chain ligand is usually employed. For example, a common method of quantum dot synthesis uses an oleic acid ligand with a length of 2.5 nm. The main part of the ligand material used in the current quantum dot material is a long carbon chain of an alkyl group. Such a quantum dot material with a ligand whose main part is a long carbon chain of an alkyl group does not have charge transport performance, and is not conducive to the transfer of charges from a charge transport layer to the surface of a quantum dot light emitting layer. When this quantum dot material is deposited into a membrane and applied to a quantum dot light emitting device, the long-chain ligands will interact to form an insulating region, increasing the resistivity and barrier. This would mismatch the energy levels between the hole transport layer and the quantum dot light emitting layer, resulting in an imbalance in the injection of electrons and holes, and affecting the injection and transport of carriers. This would in turn reduce the carrier transmission rate and affect the luminous brightness of the overall device. This is extremely disadvantageous for the application of quantum dots in the field of optoelectronics.

Figure 1:
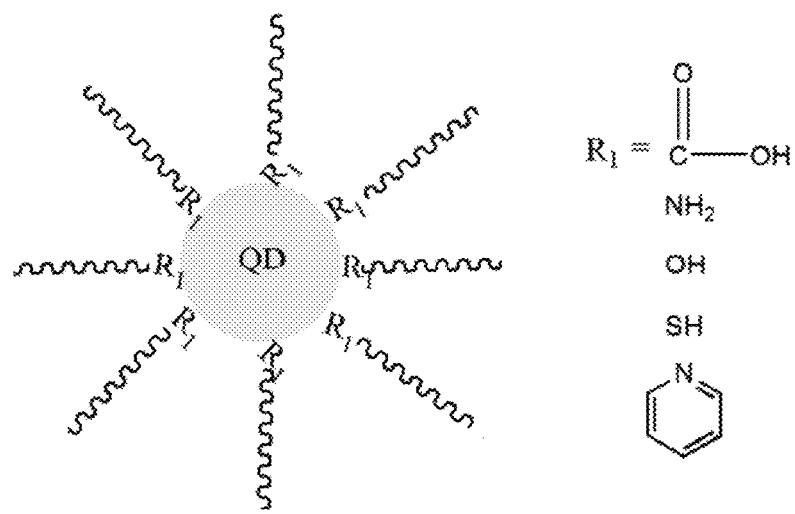
FIG. 1 shows a general structure of a quantum dot ligand.

For example, FIG. 1 shows a general structure of a quantum dot ligand. As shown in FIG. 1, due to the small size and large specific surface area of quantum dots, there are many empty orbits not occupied by electrons on the surface. Excited electrons will be captured by these empty orbits, and thus these electrons will not migrate back to emit photons, causing fluorescence quenching. Therefore, in the application of quantum dots, ligands are generally considered to eliminate the trapping state on the surface of quantum dots and thus improve the yield of photoluminescence quantum. In the general structure of the ligand, one end has a functional group containing a lone pair of electrons, such as a carboxyl group, a mercapto group, and an amine group, etc., and the other end is used to determine the solubility and dispersion of quantum dots. The general structure is shown in FIG. 1. Generally, the raw materials used to prepare quantum dots include oleic acid, trioctylphosphine and oleylamine, etc., so that the ligands finally formed on the quantum dots have a long chain, which is also conducive to the dispersion of quantum dots. As shown in FIG. 1, 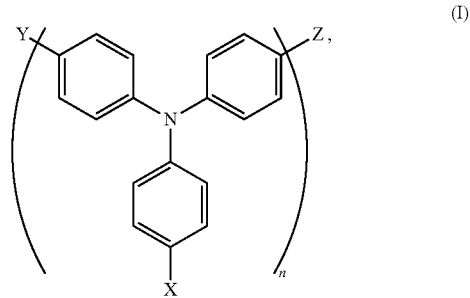 represents a long-chain alkyl group.

However, the inventors of the present disclosure also found that the reduction of the amine-based ligands on the surface of the quantum dots will reduce the quantum yield from 70% to 18%. This is because the reduction of surface ligands with a long chain structure will increase the defects on the surface of the quantum dot, and moreover the quantum dots will agglomerate. Excited electrons will be captured by some defects on the surface, causing the fluorescence quenching. Accordingly, ligand protection or ligand exchange is very important in the application of quantum dots.

The inventors of the present disclosure have designed a triphenylamine-based ligand material with a charge-transporting property through many experiments, and have subjected the triphenylamine-based small molecule to a substitution reaction. It is then used in a quantum dot light emitting layer, and further used in a quantum dot light emitting device. Compared with the current quantum dot ligands, using small molecules or polymer materials based on triphenylamine as a quantum dot ligand allows the energy level of the quantum dot surface to be adjusted, and allows the injection balance of electrons and holes in quantum dot light emitting devices to be adjusted for increasing the efficiency of quantum dot light emitting devices.

At least one embodiment of the present disclosure provides a quantum dot ligand of general formula (I),

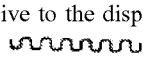

wherein n is 1, 2, 3, or 4; two of X, Y, and Z are G1 and G2 groups, respectively, and the remaining one is selected from the group consisting of G1 group, G2 group, and hydrogen, wherein the G1 group, for each occurrence, is independently selected from $-(CH_2)_m-L-(CH_2)_n-R^1$, wherein $R^1$ is a coordination group, m is 0 to 6, n is 0 to 6, and L is a divalent group or absent; the G2 group, for each occurrence, is independently selected from a $C_{4-20}$ alkyl having more than 4 carbon atoms in the carbon chain. When the general formula (I) contains two or more X's, they may be the same or different.

For example, the quantum dot ligand having the general formula (I) is mixed with quantum dots and subjected to ligand exchange to form a quantum dot material. After the formed quantum dot material is used for a quantum dot light emitting layer of a quantum dot light emitting device, the injection balance of electrons and holes can be adjusted for increasing the efficiency of the quantum dot light emitting device. Moreover, by using triphenylamine as the basic unit and replacing the groups thereon with X group, Y group, and Z group, it can be used as a quantum dot ligand through overall cooperation and can enhance the solubility of the quantum dot material.

For example, the number of triphenylamine units is 1, 2, 3, or 4. When the number of triphenylamine units is greater than 4, the steric hindrance will increase and the ligand coverage on the surface of quantum dots will be affected. By limiting the number of triphenylamine units, the HOMO level and LUMO level of the ligand units can be adjusted. Therefore, after being combined with quantum dots, the formed quantum dot ligand makes the quantum dot light emitting layer more conducive to the transport of hole carriers, which can improve the carrier injection balance in the QLED device. That is, the transport rate of hole carriers can be controlled by the number of triphenylamine units.

For example, the G2 group can play a role in enhancing solubility, and a $C_{4-20}$ alkyl having a carbon chain with more than 4 carbon atoms can play a role in enhancing solubility.

For example, the choice of different ligand molecules can have a very large impact on the quantum yield, the fluorescence performance, and the compatibility with the matrix of quantum dots. There are generally two methods for ligand modification on the surface of quantum dots. One method is to use a ligand exchange reaction to coordinate a specific ligand to the surface of the quantum dot, and the other is to use a graft reaction to graft a specific ligand to the surface of the quantum dot. The embodiments of the present disclosure are mainly realized by a ligand exchange reaction.

For example, the ligand exchange reaction uses ligands with higher coordination binding energy to replace ligands with lower coordination binding energy, and the reaction can be completed in one step. For example, the coordination binding energies of groups are ranked as follows: phosphoric acid group>carboxyl group>alkylthio group>phosphine oxide>amine group>hydroxyl group. However, due to the steric hindrance effect of the original ligand, the target ligand may not be able to effectively replace the original ligand in the ligand exchange. Therefore, in some ligand exchange reactions, ligands with a short molecular chain are needed as an intermediate ligand. In other words, the original ligand is first replaced by an intermediate ligand having weak coordination binding energy, and then the intermediate ligand is effectively replaced by the target ligand. This method has a higher replacement efficiency. For example, although the coordination ability of trioctylphosphine oxide is stronger than that of pyridine, the trioctylphosphine oxide on the surface of quantum dots can be replaced by dissolving a small amount of cadmium selenide quantum dots with trioctylphosphine oxide as a ligand in a large amount of pyridine. The cadmium selenide quantum dots obtained in this way can be regarded as bare quantum dots, so that the target ligand can be more efficiently coordinated to the surface of the quantum dot.

For example, the ligands of quantum dots themselves are in a dynamic adsorption-desorption equilibrium process. After adding a large amount of an exchange ligand, the equilibrium will move in the direction of adsorbing the exchange ligand. If the original ligand of the quantum dots is an oleic acid ligand, the equilibrium of the oleic acid ligand will move in the direction of desorption.

For example, in the quantum dot ligand of the general formula (I),

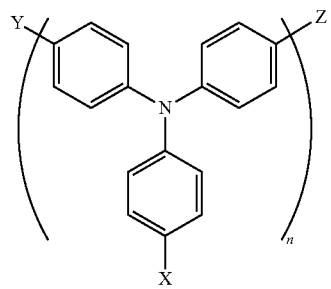

(I)

n is 1, 2, 3, or 4; two of X, Y, and Z are G1 group and G2 group, respectively, and the remaining one is selected from the group consisting of G1 group, G2 group, and hydrogen, wherein the G1 group, for each occurrence, is independently selected from $-(CH_2)_m-L-(CH_2)_n-R^1$, wherein $R^1$ is a coordination group, m is 0 to 6, n is 0 to 6, and L is a divalent group or absent; the G2 group, for each occurrence, is independently selected from a $C_{4-20}$ alkyl having a carbon chain with more than 4 carbon atoms.

For example, the coordination group $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group, wherein the amine group may include a primary amine group and a secondary amine group, etc., such as pyridyl and pyrimidinyl.

For example, when L is a divalent group, L may be O, NH, S, or the like.

As a divalent group, L may also be a divalent hydrocarbon group, for example, an aliphatic group having 1 to 12 carbon atoms (e.g., methylene, ethylene, propylene, methylethylene, 2,2-dimethylethylene, butylene, methylpropylene, 1,4-butylene and 1,6-hexylene), an alicyclic group having 3 to 6 carbon atoms (e.g., cyclohexylene), and an aromatic group having 6 to 12 carbon atoms (e.g., phenylene, 2-methylphenylene, 3-methylphenylene, and biphenylene), etc. When L is a divalent hydrocarbon group, L may have a branch chain and $-(CH_2)_n-R^1$ may be connected to the branch chain of L or may not be connected to the branch chain of L. When L is a divalent hydrocarbon group, L may be substituted with a substituent(s) such as oxo, halogen, CN, mercapto, hydroxyl, $C_{1-6}$ alkyl, $C_3-C_6$-cycloalkyl and the like.

The absence of L means that $-(CH_2)_m-$ is directly connected to $-(CH_2)_n-R^1$.

For example, in this embodiment, the value range of m is limited to an integer of 0 to 6. When m is 0, and L is absent, and n is 0, there is no carbon atom between the coordination group $R^1$ and the aromatic ring, that is, the coordination group $R^1$ is directly connected to the aromatic ring. When m is not 0, there is at least one carbon atom between the coordination group $R^1$ and the aromatic ring, and heteroatoms such as oxygen, nitrogen, and sulfur are not directly connected to the aromatic ring. In this way, the HOMO energy level can be limited in the desired range.

For example, the quantum dot ligand provided by at least one embodiment of the present disclosure has a molecular structure of

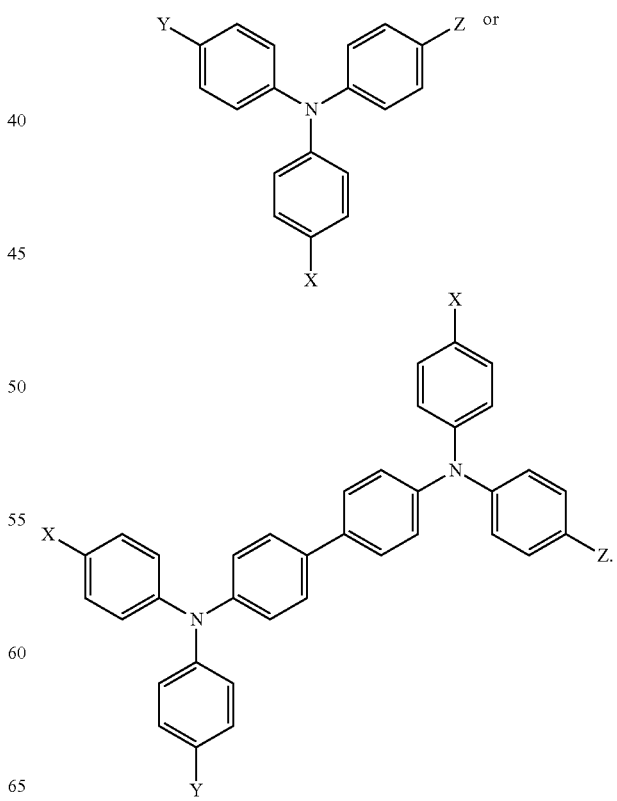

In

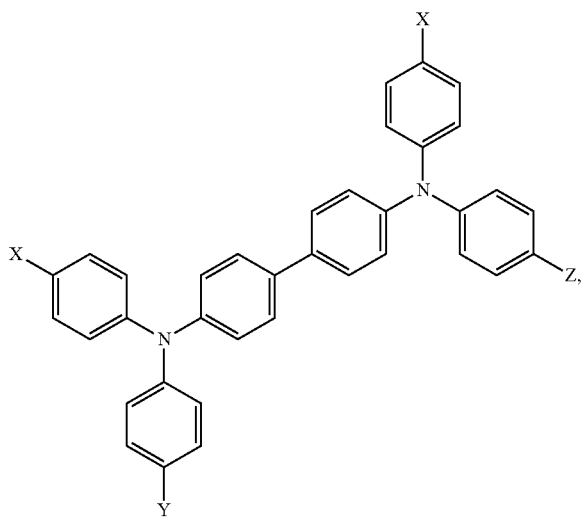

two X's may be the same or different.

For example, in the quantum dot ligand provided by at least one embodiment of the present disclosure, G1 is —$(CH_2)_m$-L-$(CH_2)_n$—$R^1$, wherein L is absent or selected from the group consisting of O, NH, S, a linear $C_1$-$C_6$-alkylene, a branched $C_3$-$C_6$-alkylene, $C_3$-$C_6$-cycloalkylene or $C_6$-$C_{12}$ arylene, and L is optionally substituted with a substitutent(s) selected from the group consisting of oxo, halogen, CN, mercapto, hydroxyl, a $C_{1-6}$ alkyl, a $C_4$-$C_6$-cycloalkyl, and an aryl of 6 to 12 carbon atoms; $R^1$ is selected from the group consisting of a mercapto group (—SH), a hydroxyl group (—OH), an amine group, an amino group (—$NH_2$), a carboxyl group (—COOH), a phosphine group, a phosphine oxide group, a phosphoric acid group (—$PO_4H$), a phosphoric acid ester group, and a sulfonic acid group (—$SO_3H$); m is an integer of 1 to 6; and n is an integer of 0 to 6.

As used herein, the amine group refers to an organic functional group obtained by replacing the hydrogen atom of ammonia with an alkyl group, for example, pyridyl.

For example, in one embodiment, G1 is —$(CH_2)_m$-L-$(CH_2)_n$—$R^1$, wherein m is an integer of 1 to 6, n is an integer of 0 to 6, and $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

For example, in one embodiment, G1 is —$(CH_2)_m$-L-$(CH_2)_n$—$R^1$, wherein m is 1, n is an integer of 0 to 6, and $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

For example, in one embodiment, the absence of L means that G1 is —$(CH_2)_m$—$(CH_2)_n$—$R^1$, wherein m is an integer of 0 to 6 and n is an integer of 0 to 6.

For example, when L is a branched $C_3$-$C_6$-alkyl-, —$(CH_2)_n$—$R^1$ may be attached to the branch chain.

For example, in one embodiment, G1 is —$(CH_2)_2$-L-$(CH_2)_2$-$R^1$, wherein $R^1$ is $NH_2$ and L is O, NH, S, or $CH_2$.

For example, in one embodiment, G1 is —$CH_2$-L-$(CH_2)_2$—$R^1$, wherein $R^1$ is $NH_2$, and L is O, NH, S, or $CH_2$.

For example, in yet another embodiment, G1 is —$R^1$, and $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

For example, in the quantum dot ligand provided by at least one embodiment of the present disclosure, the G2 group is a linear alkyl group with 4 to 8 carbon atoms; or the G2 group is a branched alkyl group with 6 to 12 carbon atoms in the main chain (the longest carbon chain in the G2 group is defined as the main chain) and 2 to 6 carbon atoms in the branch chain. If the content of carbon atoms in the G2 group is too high, there will be a problem that the carbon chain affects carrier transport. If the content of carbon atoms in the G2 group is too low, the problem of poor solubility of quantum dots will occur.

For example, G2 includes n-butyl, n-pentyl, n-hexyl, n-heptyl, n-octyl, 2-ethyl-hexyl, 3-ethyl-hexyl, 4-ethyl-hexyl, 2-ethyl-heptyl, 3-ethyl-heptyl, 4-ethyl-heptyl, 5-ethyl-heptyl, and so on. In some embodiments, G2 is 2-ethyl-hexyl.

For example, the quantum dot ligand has a molecular structure of:

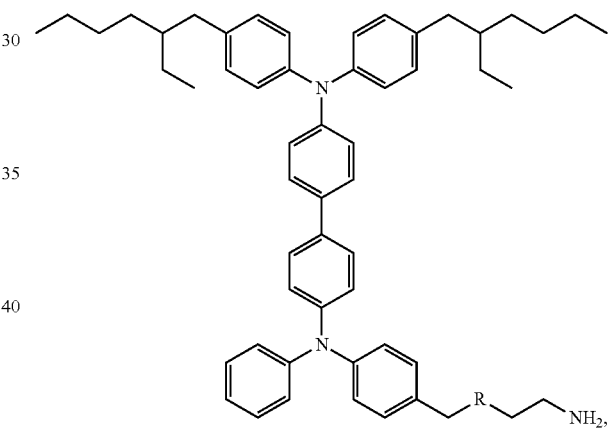

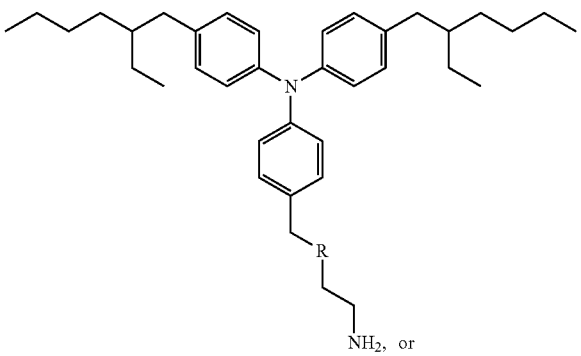

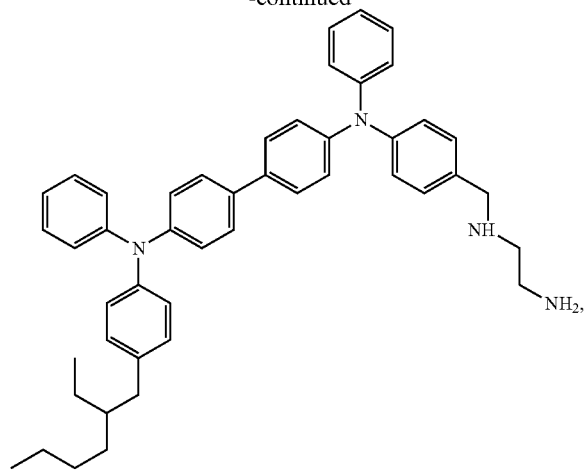

wherein R is O, NH, S or CH$_2$.

For example, when R is CH$_2$, the quantum dot ligand can have a molecular structure of:

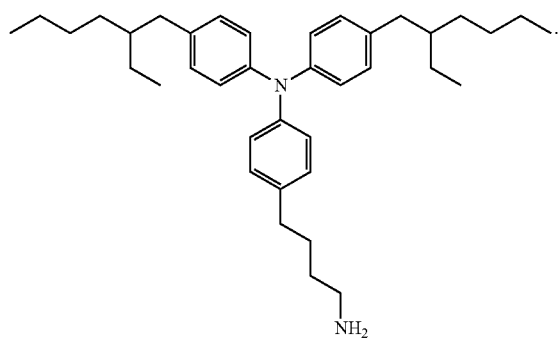 [SMILES: CCCCC(CC)Cc1ccc(N(c2ccc(CCCCN)cc2)c2ccc(CC(CC)CCCC)cc2)cc1]

For another example, the quantum dot ligand can have a molecular structure of:

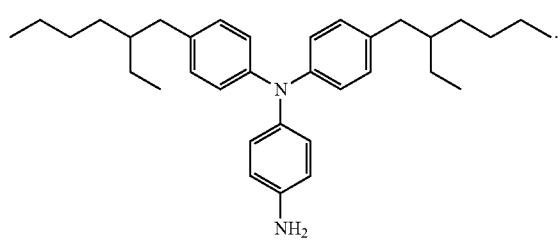 [SMILES: CCCCC(CC)Cc1ccc(N(c2ccc(N)cc2)c2ccc(CC(CC)CCCC)cc2)cc1]

At least one embodiment of the present disclosure includes a method of preparing the above quantum dot ligands.

For example, the process of preparing the above quantum dot ligand A is described as follows.

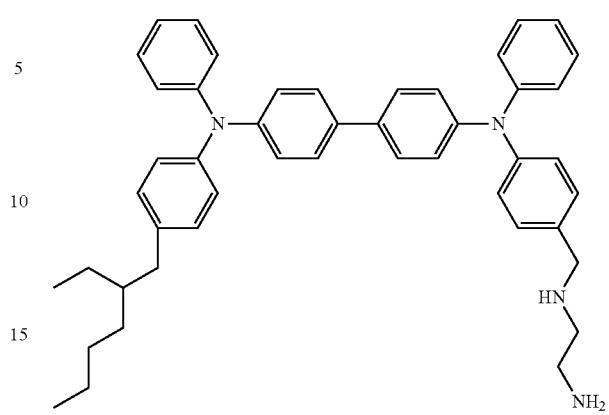

Ligand molecule A 10 mmol of Bromotriphenylamine was placed in a flask and dissolved with 50 mL of tetrahydrofuran. After dissolution, 10.5 mmol of n-butyl lithium was added to the solution, and the reaction was carried out at a low temperature for 2 hours. 15 mmol of 2-ethylbromohexane was then added, and the reaction was carried out at a low temperature for another 2 hours and then at room temperature for 12 hours. After the reaction was completed, the product A1 was obtained by extraction, washing and column chromatography. The corresponding reaction equation is:

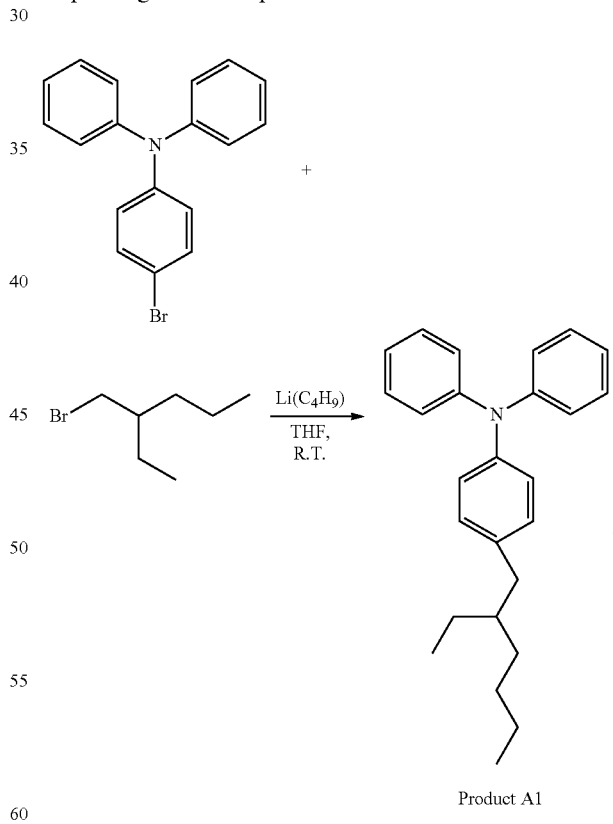

Product A1

For example, the processes of extraction, washing and column chromatography include pouring the reaction product into water, extracting by adding dichloromethane, drying by adding anhydrous magnesium sulfate after the extraction, and then carrying out column chromatography by eluent with a molar ratio of petroleum ether:dichloromethane=3:1.

For example, the low temperature may be a temperature below −25° C.

10 mmol of product A1 and 10.5 mmol of N-bromosuccinimide were dissolved in 50 mL of tetrahydrofuran and stirred at room temperature for 12 hours. The product A2 was then obtained by extraction, washing, and column chromatography.

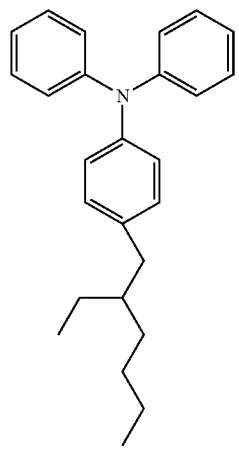

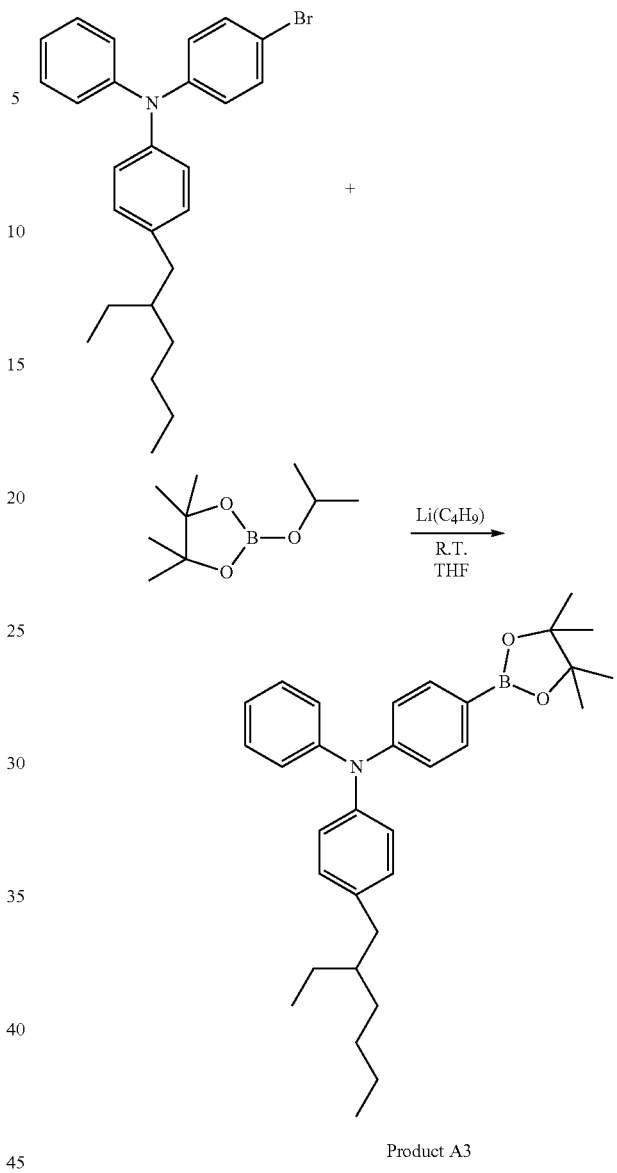

Product A2

For example, in this step, the processes of extraction, washing and column chromatography include pouring the reaction product into water, extracting by adding dichloromethane, drying by adding anhydrous magnesium sulfate after the extraction, and then carrying out column chromatography by eluent with a molar ratio of petroleum ether:dichloromethane=3:1.

10 mmol of product A2 was placed in a flask and dissolved in 50 mL of tetrahydrofuran. 10.5 mmol of n-butyllithium was added to the formed solution and reacted at a low temperature for 2 hours. 12 mmol of boron ester was added, and the reaction was carried out at a low temperature for 2 hours and then at room temperature for 12 hours. After the reaction was completed, the product A3 was obtained by extraction, washing and column chromatography.

Product A3

10 mmol of bromotriphenylamine was dissolved in a mixed solution of 20 mL of N,N-dimethylformamide and 30 mL of dichloroethane. 12 mmol of phosphorus oxychloride was then added. The reaction solution was heated to 90° C. and reacted for 12 hours. After the reaction was completed, the product A4 was obtained by extraction, washing and column chromatography.

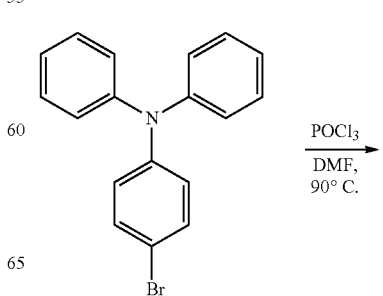

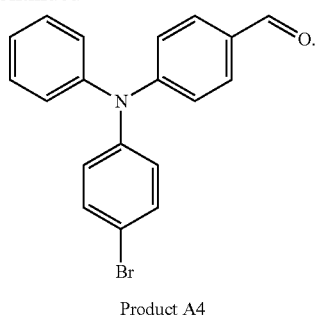

Product A4

For example, in this step, the processes of extraction, washing and column chromatography can refer to the processes described above, and will not be repeated here.

10.5 mmol of product A3 and 10 mmol of product A4 were dissolved together in 50 mL of toluene to form a mixed solution, to which 100 mg of tetra(triphenylphosphino)palladium and 500 μl of methyltrioctylammonium chloride were then added. The reaction solution was heated at reflux for 12 hours, and then the reaction was stopped. The product A5 was obtained by extraction, washing and column chromatography.

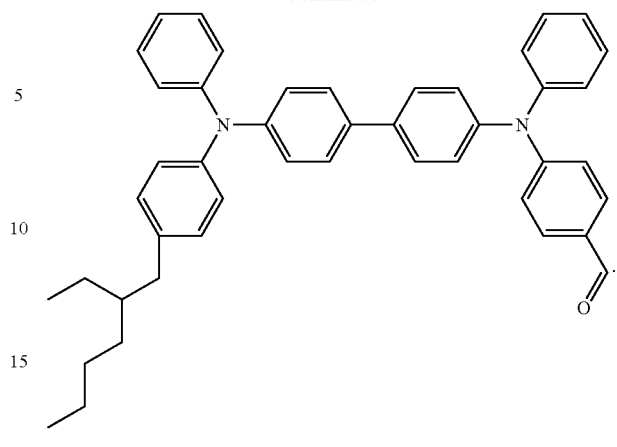

Product A5

For example, in this reaction step, tetra(triphenylphosphino)palladium is used as a catalyst, and methyltrioctylammonium chloride is used as a base.

1 mmol of product A5 was dissolved in a mixed solution of 8 mL of ethanol and 2 mL of tetrahydrofuran. 6 mmol of ethylenediamine was dissolved in a mixed solution of 4 mL of ethanol and 1 mL of tetrahydrofuran, to which 100 mg of anhydrous magnesium sulfate was then added. The dissolved product E was added dropwise to the ethylenediamine solution. The reaction solution was reacted at a low temperature for 2 hours and then reacted at room temperature for 12 hours. 1.05 mmol of sodium borohydride was then added. The mixture was reacted for 1 hour, and then the reaction was stopped. The final product, ligand molecule A, was obtained by extraction, washing, and column chromatography.

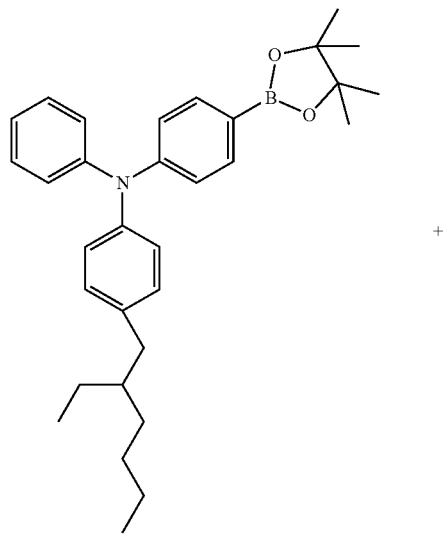

+

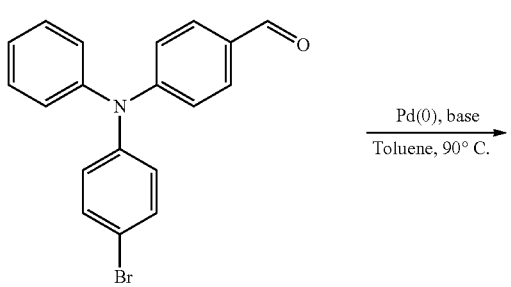

Pd(0), base
Toluene, 90° C.

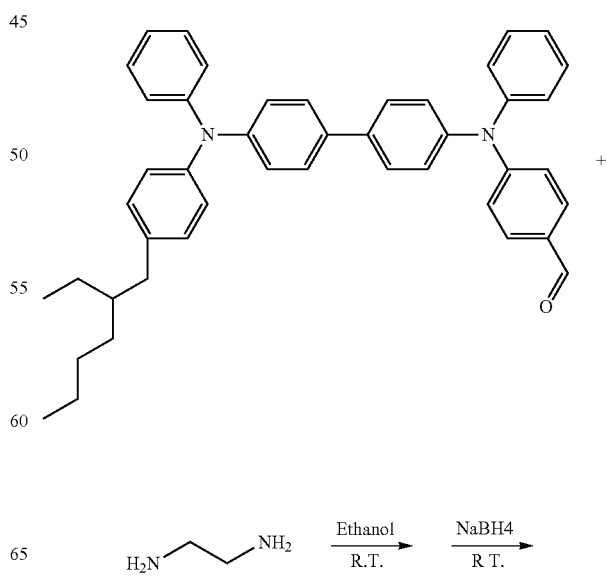

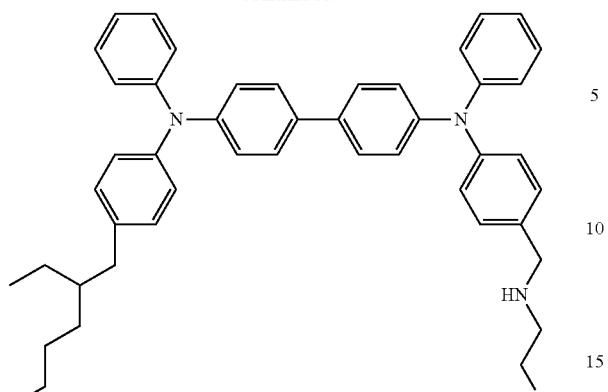

Ligand molecule A

For example, the process of preparing the above quantum dot ligand molecule B is described as follows.

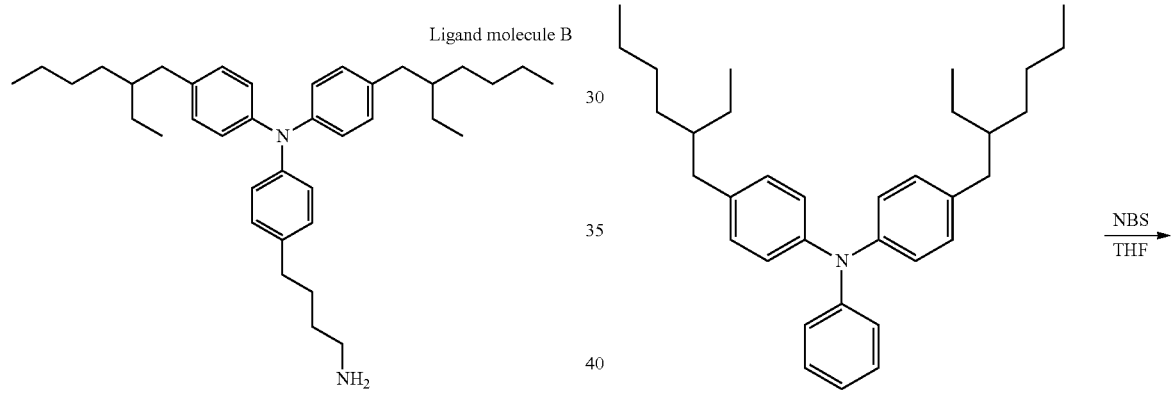

Ligand molecule B 10 mmol of dibromotriphenylamine was placed in a flask, and dissolved with 50 mL of tetrahydrofuran. To the mixture was added 21 mmol of n-butyllithium. The reaction solution was reacted at a low temperature for 2 hours. 30 mmol of 2-ethylhexane was then added. The reaction solution was reacted at a low temperature for 2 hours and then reacted at room temperature for 12 hours. After the reaction was completed, the product B1 was obtained by extraction, washing and column chromatography.

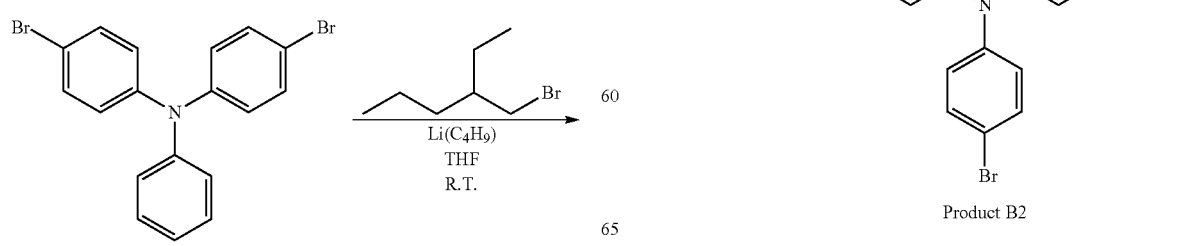

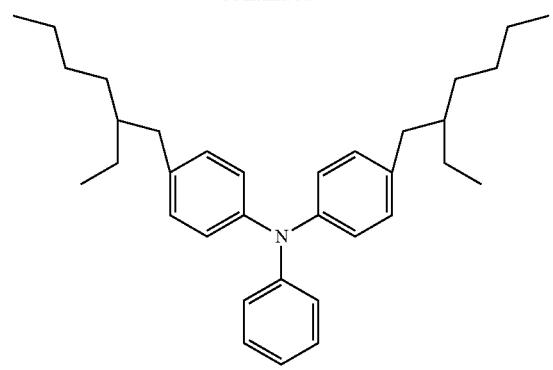

Product B1

10 mmol of product B1 and 10.5 mmol of N-bromosuccinimide were dissolved together in 50 mL of tetrahydrofuran, and stirred at room temperature for 12 hours. The product B2 was then obtained by extraction, washing, and column chromatography.

Product B2

10 mmol of product B2 was placed in a flask, and dissolved with 50 mL of tetrahydrofuran. 10.5 mmol of n-butyllithium was added to the mixture, which was then reacted at a low temperature for 2 hours. 15 mmol of bromopropylamine was then added. The reaction solution was reacted at a low temperature for 2 hours and then reacted at room temperature for 12 hours. After the reaction was completed, the product, ligand molecule B, was obtained by extraction, washing and column chromatography.

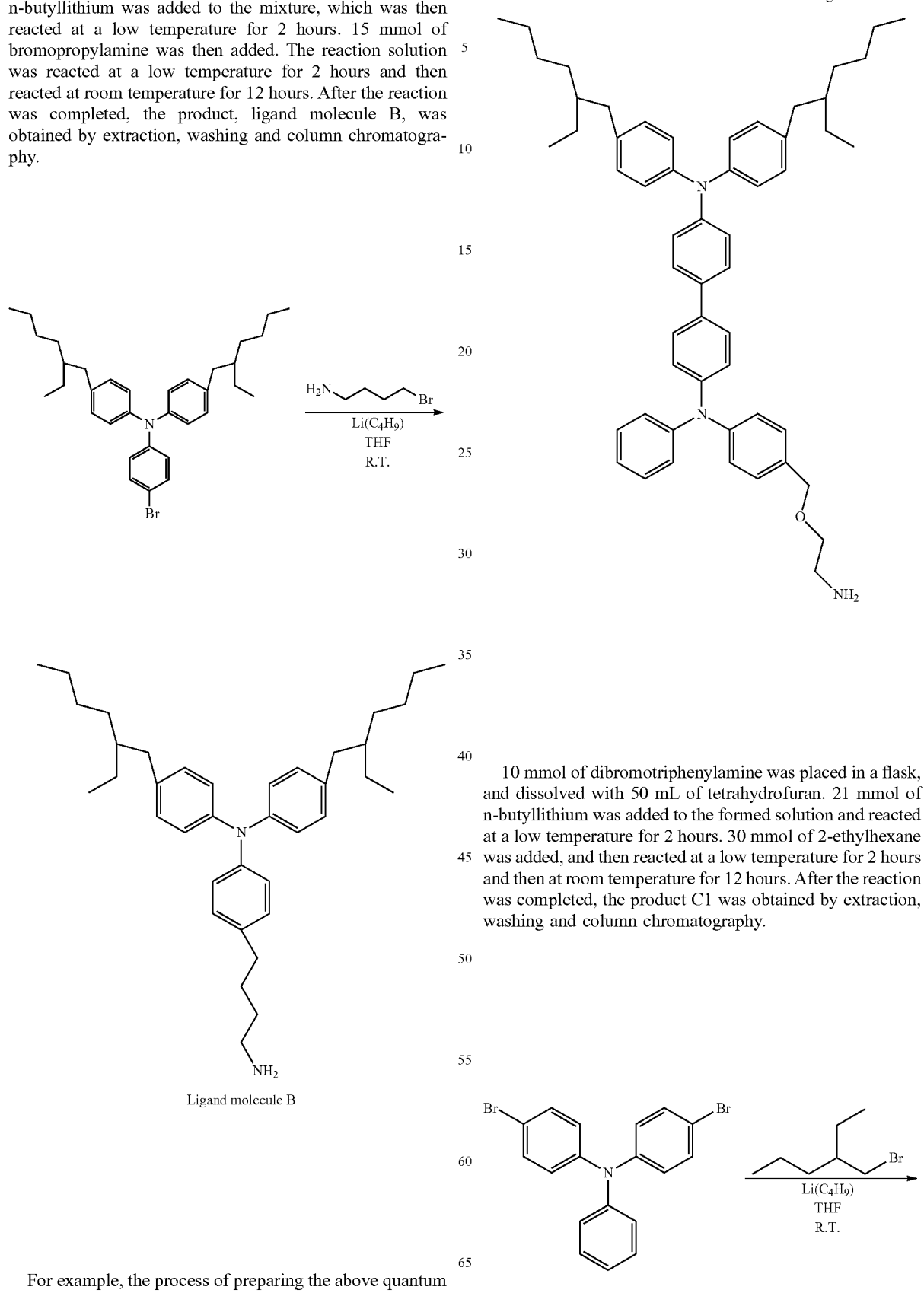

10 mmol of dibromotriphenylamine was placed in a flask, and dissolved with 50 mL of tetrahydrofuran. 21 mmol of n-butyllithium was added to the formed solution and reacted at a low temperature for 2 hours. 30 mmol of 2-ethylhexane was added, and then reacted at a low temperature for 2 hours and then at room temperature for 12 hours. After the reaction was completed, the product C1 was obtained by extraction, washing and column chromatography.

For example, the process of preparing the above quantum dot ligand C is described as follows.

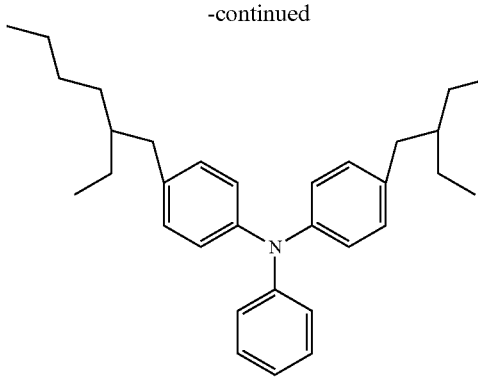

Product C1

10 mmol of product C1 and 10.5 mmol of N-bromosuccinimide were dissolved together in 50 mL of tetrahydrofuran, and stirred at room temperature for 12 hours. The product C2 was obtained by extraction, washing, and column chromatography.

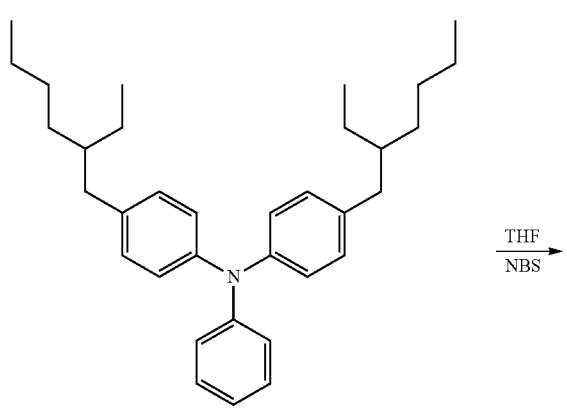

Product C2

10 mmol of product C2 was placed in a flask, and dissolved with 50 mL of tetrahydrofuran. 10.5 mmol of n-butyllithium was added to the solution, and reacted at a low temperature for 2 hours. 12 mmol of boron ester was added and reacted at a low temperature for 2 hours and then at room temperature for 12 hours. After the reaction was completed, the product C3 was obtained by extraction, washing and column chromatography.

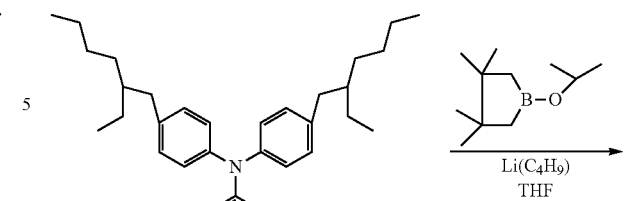

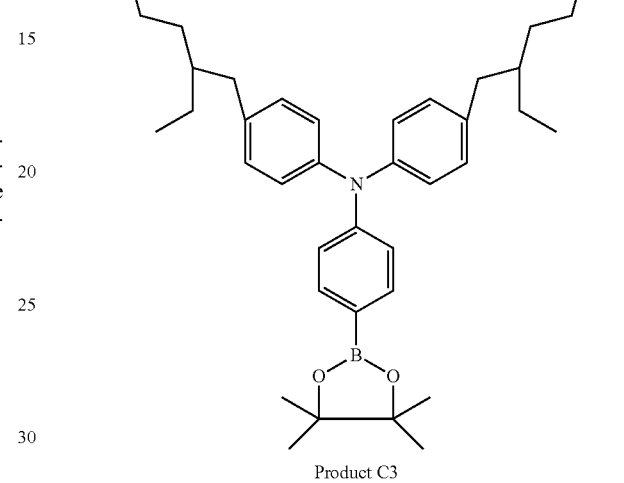

Product C3

10 mmol of bromotriphenylamine was dissolved in a mixed solution of 20 mL of N,N-dimethylformamide and 30 mL of dichloroethane, to which 12 mmol of phosphorus oxychloride was then added. The reaction solution was heated to 90° C. and reacted for 12 hours. After the reaction was completed, the product C4 was obtained by extraction, washing and column chromatography.

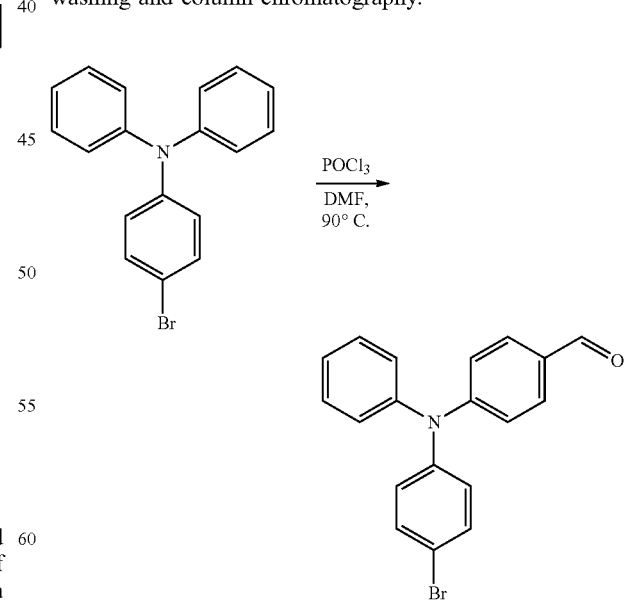

Product C4

10.5 mmol of product C3 and 10 mmol of product C4 were dissolved in 50 mL of toluene, to which 100 mg of tetra(triphenylphosphino)palladium and 500 µl of methyltrioctylammonium chloride were then added. The reaction solution was heated at reflux for 12 hours, and then the reaction was stopped. The product C5 was obtained by extraction, washing and column chromatography.

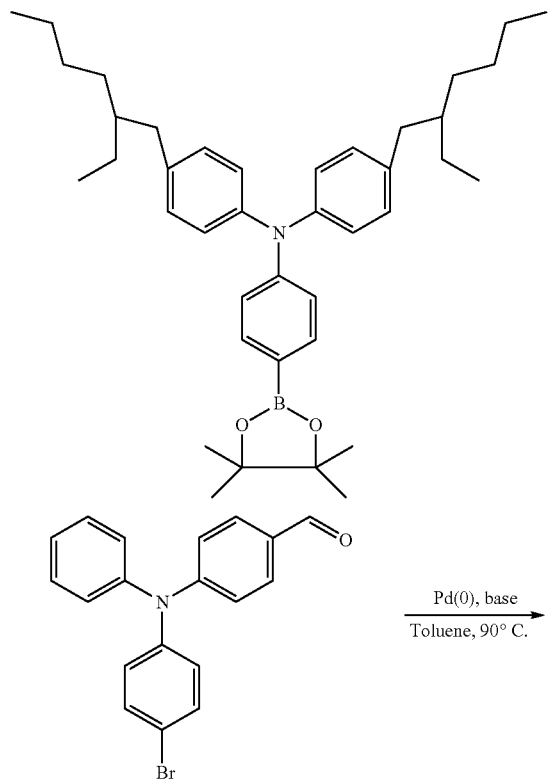

1 mmol of product C5 was dissolved in a mixed solution of 8 mL of ethanol and 2 mL of tetrahydrofuran. 6 mmol of ethylenediamine was dissolved in a mixed solution of 4 mL of ethanol and 1 mL of tetrahydrofuran, to which 100 mg of anhydrous magnesium sulfate was then added. The dissolved product E was slowly added dropwise to the ethylenediamine solution and reacted at a low temperature for 2 hours and then at room temperature for 12 hours. 1.05 mmol of sodium borohydride was added. The mixture was reacted for 1 hour, and then the reaction was stopped. The final product, ligand molecule C, was obtained by extraction, washing, and column chromatography.

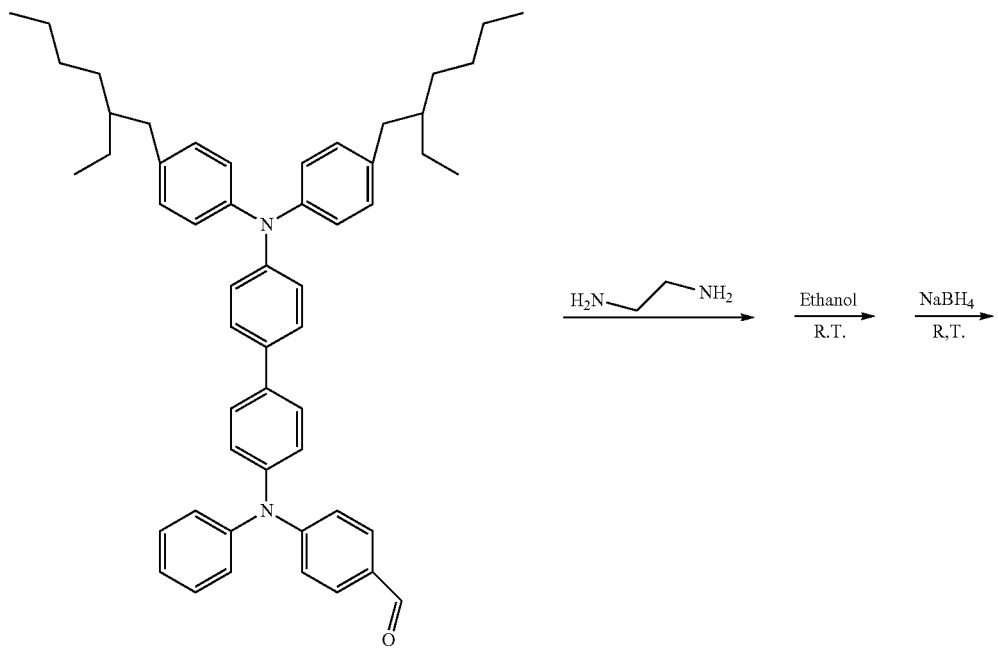

-continued

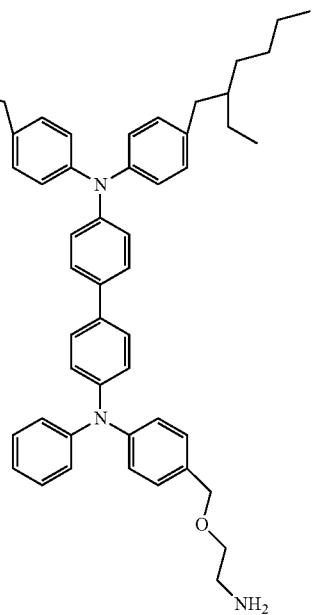

Ligand molecule C

At least one embodiment of the present disclosure also provides a quantum dot material, including a quantum dot and the quantum dot ligand as described in any one of the above embodiments.

For example, in the quantum dot material provided by at least one embodiment of the present disclosure, the quantum dot includes CdS, CdSe, CdTe, ZnSe, InP, PbS, $CsPbCl_3$, $CsPbBr_3$, $CsPhI_3$, CdS/ZnS, CdSe/ZnS, ZnSe, InP/ZnS, PbS/ZnS, $CsPbCl_3$/ZnS, $CsPbBr_3$/ZnS or $CsPhI_3$/ZnS.

For example, when the quantum dot material with the above quantum dot ligand is used in a quantum dot light emitting layer of a quantum dot light emitting device, the energy level of the surface of the quantum dot can be adjusted, and the injection balance of electrons and holes in the quantum dot light emitting device can be adjusted to increase the efficiency of the quantum dot light emitting device.

At least one embodiment of the present disclosure also provides a method of preparing a quantum dot material, including mixing a quantum dot and the quantum dot ligand provided by any of the above embodiments.

For example, in the preparation method provided by at least one embodiment of the present disclosure, mixing a quantum dot ligand with a quantum dot to form a quantum dot material includes: dissolving the synthesized quantum dot ligand in a non-polar solvent to form a solution A, dissolving the quantum dot in the solution A, reacting at room temperature, then precipitating with a polar solvent, centrifuging and then removing the supernatant, then dissolving with a non-polar solvent, and then repeating the above processes of precipitation, centrifuging to remove the supernatant, and dissolving.

For example, in the preparation method provided by at least one embodiment of the present disclosure, the non-polar solvent is selected from the group consisting of n-octane, heptane, hexane, decane, nonane, toluene, xylene, and chlorobenzene; and the polar solvent is selected from the group consisting of ethanol, butyl formate, butyl propionate, methanol, isopropanol, butanol, and tetrahydrofuran.

For example, in the preparation method provided by at least one embodiment of the present disclosure, the non-polar solvent is a mixed solvent, such as a combination of any one of n-octane, heptane, hexane, decane and nonane and any one of toluene, xylene and chlorobenzene.

For example, in the preparation method provided by at least one embodiment of the present disclosure, mixing the quantum dot ligand with the quantum dot to form a quantum dot material includes: dissolving the synthesized quantum dot ligand in a mixed solvent of n-octane/toluene with a volume ratio of n-octane:toluene of from 1:0.2 to 1:10 to obtain a solution A with a concentration of 10 mg/mL to 100 mg/mL, dissolving the quantum dot in the solution A with a mass ratio of quantum dot:ligand molecule of from 1:0.2 to 1:10 for ligand exchange, exchanging at room temperature for 20 minutes to 1 hour, and then precipitating with ethanol, centrifuging and removing the supernatant, then dissolving with octane, then precipitating with ethyl acetate, centrifuging and removing the supernatant, then dissolving with octane, then precipitating with ethyl acetate, and finally dissolving with octane to form 2 mg/mL to 10 mg/mL of a quantum dot solution.

For example, in the preparation method provided by at least one embodiment of the present disclosure, mixing the quantum dot ligand with the quantum dot to form a quantum dot material includes: dissolving the synthesized quantum dot ligand in a mixed solvent of n-octane/toluene with a volume ratio of n-octane:toluene of 1:0.5 to obtain a solution A with a concentration of 50 mg/mL, dissolving the quantum dot in the solution A with a mass ratio of quantum dot:ligand molecule of 1:5 for ligand exchange, exchanging at room temperature for half an hour, and then precipitating with ethanol, centrifuging and removing the supernatant, dissolving with octane, then precipitating with ethyl acetate, centrifuging and removing the supernatant, then dissolving with octane, then precipitating with ethyl acetate, and finally dissolving with octane to form 5 mg/mL of a quantum dot solution.

For example, in the preparation method provided by at least one embodiment of the present disclosure, mixing the quantum dot ligand with the quantum dot to form a quantum dot material includes: dissolving the synthesized quantum dot ligand in xylene to obtain a solution A, dissolving the quantum dot in the solution A with a mass ratio of quantum dot:ligand molecule of 1:3 for ligand exchange, exchanging at room temperature for half an hour, and then precipitating with ethanol, centrifuging and removing the supernatant, then dissolving with xylene, then precipitating with ethyl acetate, centrifuging and removing the supernatant, dissolving with xylene, then precipitating with ethyl acetate, and finally dissolving with xylene to form 40 mg/mL of a quantum dot solution.

Figure 2:
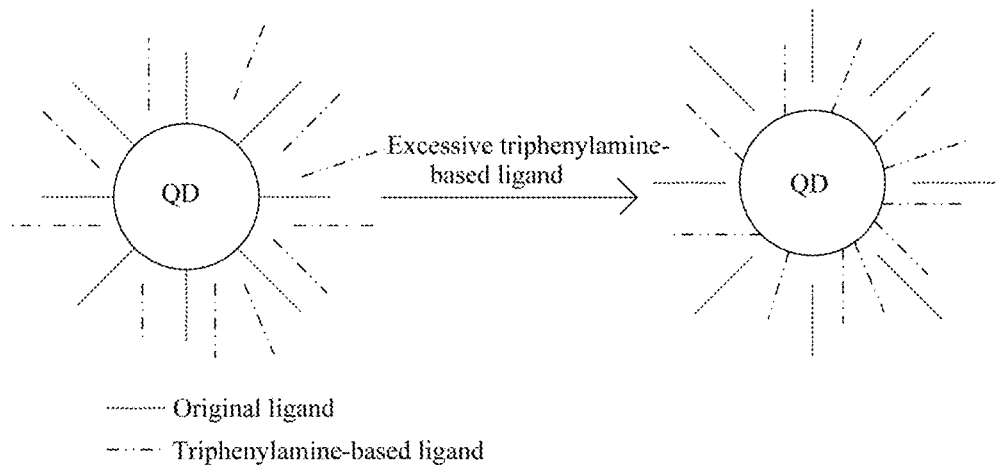
FIG. 2 is a schematic diagram of an exchange process of ligand molecules on the surface of a quantum dot provided by an embodiment of the present disclosure.

For example, FIG. 2 is a schematic diagram of the exchange process of ligand molecules on the surface of a quantum dot provided by an embodiment of the present disclosure. As shown in FIG. 2, in the case of excessive triphenylamine-based ligand molecules, the triphenylamine-based ligand molecules can replace the original ligand on the surface of the quantum dot, for example, an oleic acid-based ligand molecule or an oleamine-based ligand molecule.

For example, after the preparation of the above quantum dot materials, an infrared spectrum and an XPS spectrum can be used to characterize whether the ligand is sufficiently exchanged. The quantum dot ligand molecule A is taken as an example for description below.

Ligand molecule A

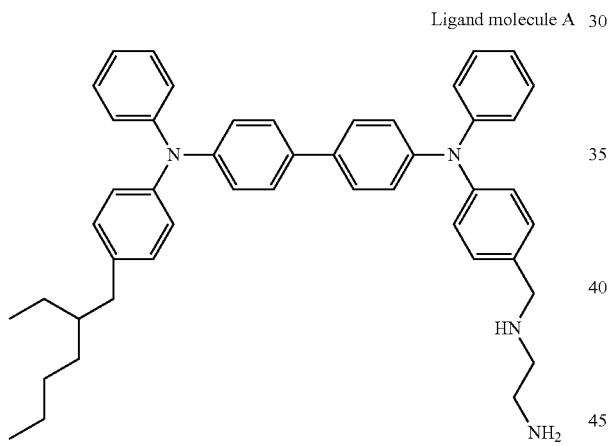

Figure 3:
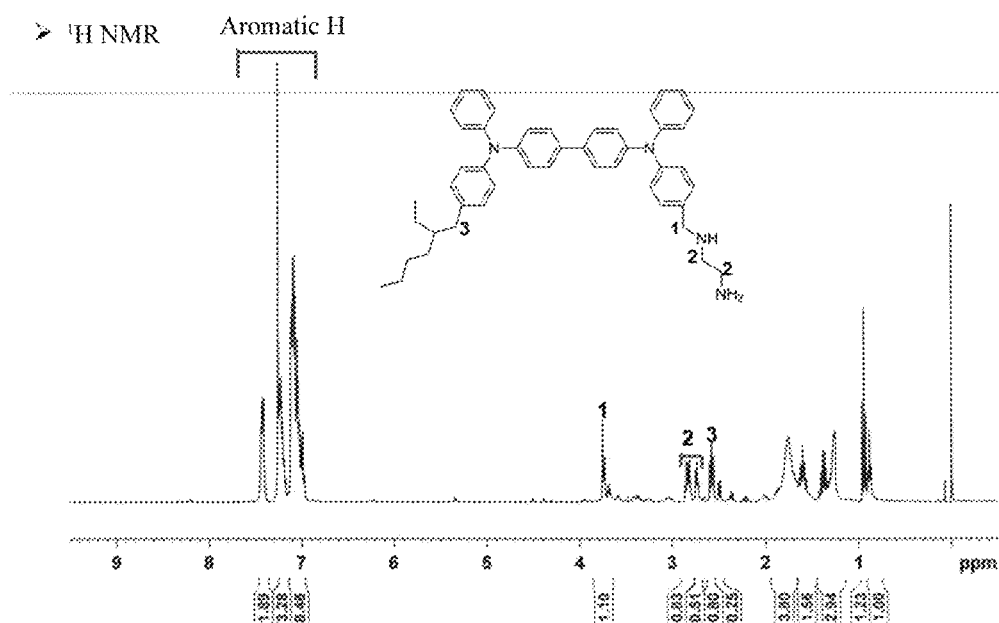
FIG. 3 is a nuclear magnetic hydrogen spectrum of ligand molecule A provided by an embodiment of the present disclosure.

For example, FIG. 3 is $^1$HNMR of ligand molecule A provided by an embodiment of the present disclosure. As shown in FIG. 2, the hydrogen of the aryl group, the hydrogen of the alkyl group, the hydrogen of the amino group and the hydrogen of the imino group are all reflected. The hydrogens in the NMR spectrum in FIG. 3 correspond to the hydrogens in the structural formula of the ligand molecule A one by one. Combined with the molecular ion peak value in high-resolution mass spectrometry, it can be confirmed that the ligand molecule A is synthesized.

Figure 4:
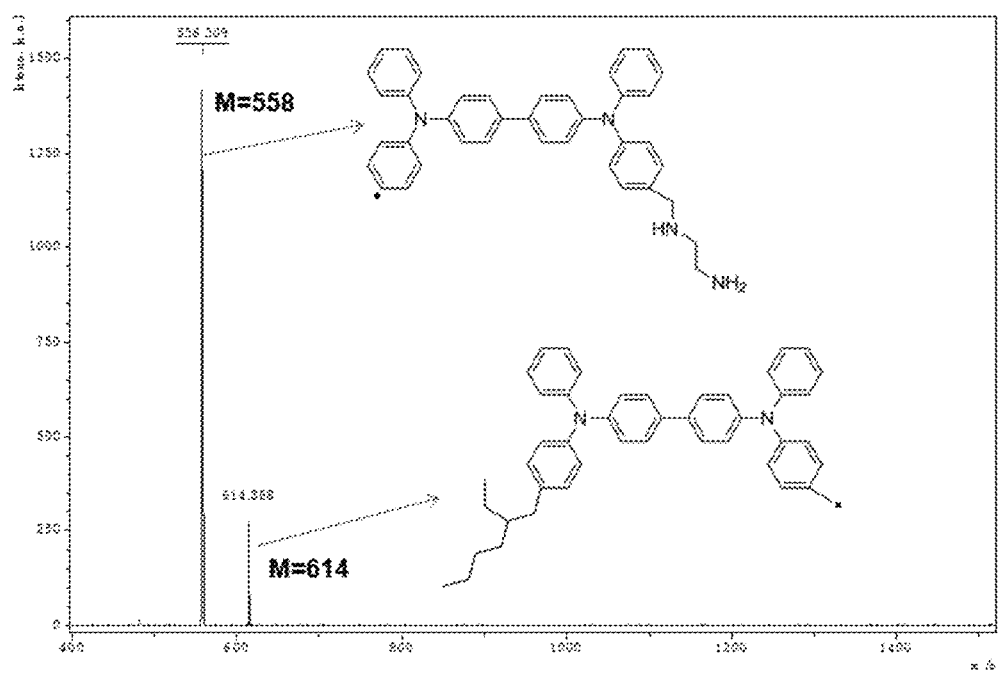
FIG. 4 is a high-resolution mass spectrogram of ligand molecule A provided by an embodiment of the present disclosure.

For example, FIG. 4 is a high-resolution mass spectrum of ligand molecule A provided by an embodiment of the present disclosure. As shown in FIG. 4, the substitutions at the X group and the Y group are both reflected.

Figure 5:
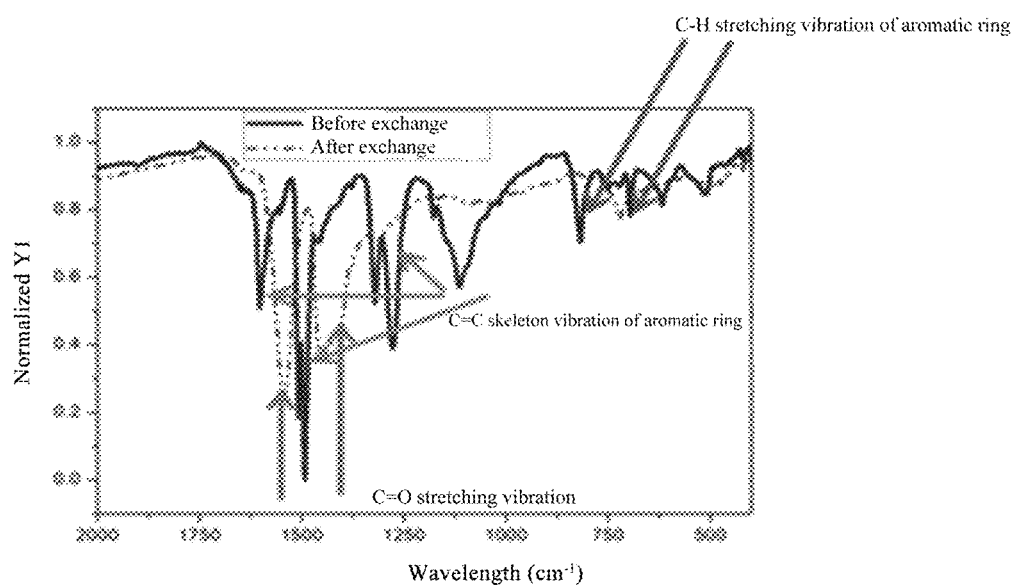
FIG. 5 shows an infrared spectrum diagram before and after quantum dot ligand exchange using ligand molecule A provided by an embodiment of the present disclosure.

For example, FIG. 5 is an infrared spectrogram before and after ligand exchange provided by an embodiment of the present disclosure. For example, infrared spectrometry characterizes the changes in functional groups of ligands on the surface of quantum dots. As shown in FIG. 5, the stretching vibration peak of C=O disappears, and the characteristic peak of the vibration of the C=C skeleton of the aromatic ring and the stretching vibration peak of the C—H of the aromatic ring newly appear. The appearance of the characteristic peaks of the aromatic ring confirms the success of ligand exchange.

Figure 6:
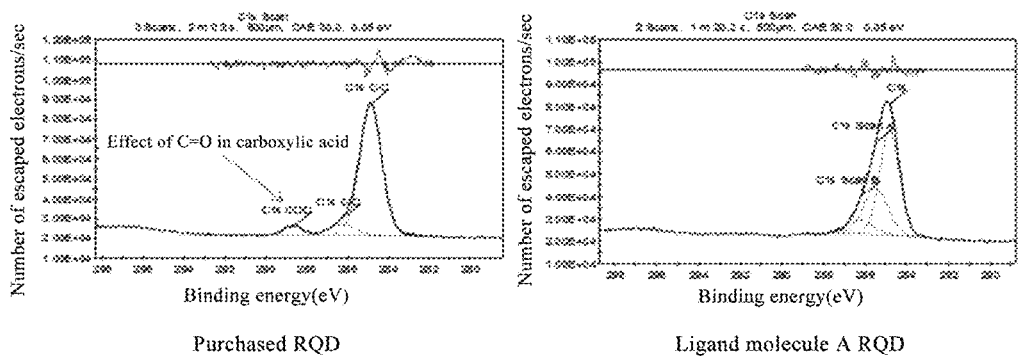
FIG. 6 shows an XPS spectrum before and after quantum dot ligand exchange using ligand molecule A provided by an embodiment of the present disclosure.

For example, FIG. 6 is an XPS spectrum before and after the exchange of a ligand molecule A provided by an embodiment of the present disclosure with quantum dots. For example, XPS elemental analysis is used to characterize the changes in elements on the surface of quantum dots. As shown in FIG. 6, the peak of the C=O interaction disappears, indicating that the ligand exchange has been completed.

Figure 7:
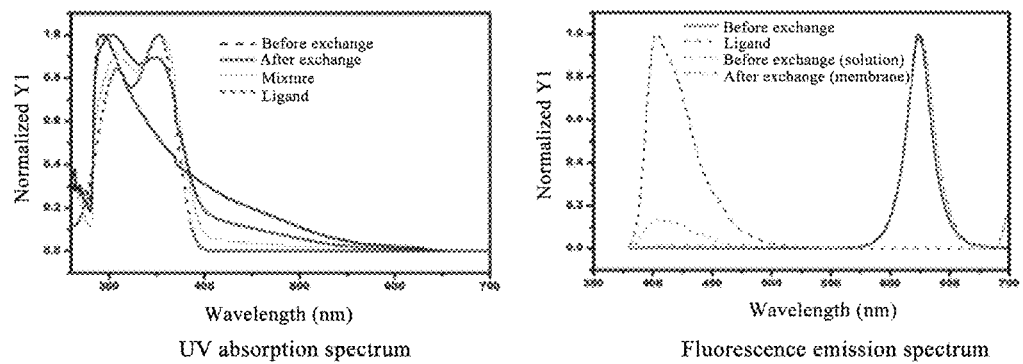
FIG. 7 shows an ultraviolet absorption spectrum and a fluorescence emission spectrum before and after quantum dot ligand exchange using ligand molecule A provided by an embodiment of the present disclosure.

For example, the optical properties of the quantum dot material are characterized by ultraviolet-visible spectrophotometer and fluorescence spectrophotometer. The ultraviolet-visible spectrophotometer is used to characterize the absorption peak position and absorption intensity of quantum dots, and can characterize the transparency of the quantum dot material in transmission mode by employing air as the background. The fluorescence spectrophotometer has two modes, one is the emission spectrum mode, which is mainly used to characterize the fluorescence intensity of quantum dots, and the other is the excitation mode, which is mainly used to characterize the range of quantum dots being excited. FIG. 7 shows an ultraviolet absorption spectrum and a fluorescence emission spectrum before and after the exchange of ligand molecule A provided by an embodiment of the present disclosure with quantum dots. As shown in FIG. 7, in the ultraviolet absorption spectrum, before ligand exchange, only one characteristic peak appears at a wavelength of about 300 nm, and after ligand exchange, characteristic peaks appear at a wavelength of about 320 nm and about 370 nm, respectively. In the fluorescence emission spectrum, before ligand exchange, no characteristic peak appears between 380 nm and 450 nm.

In the following embodiments, the preparation of a quantum dot material containing the above triphenylamine-based ligand molecules by the ligand exchange reaction is explained. For example, the selected quantum dot CdSe has oleic acid ligands on its surface after preparation. Due to the dynamic equilibrium of adsorption and desorption on the surface of cadmium selenide quantum dots, ligand exchange will occur in the presence of another ligand with a stronger coordination ability, and each bound ligand will participate in the adsorption-desorption dynamic equilibrium.

The first example: Preparation of a quantum dot material with triphenylamine-based ligand molecule A.

Ligand molecule A

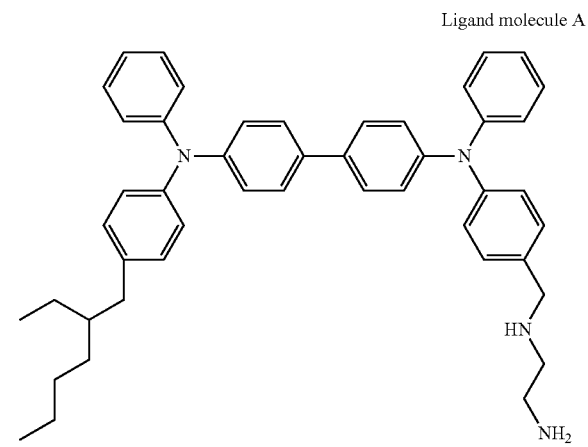 [SMILES: CCCCC(CC)Cc1ccc(N(c2ccccc2)c2ccc(-c3ccc(N(c4ccccc4)c4ccc(CNCCN)cc4)cc3)cc2)cc1]

The synthesized triphenylamine-based ligand molecule A was dissolved in a mixed solvent of n-octane/toluene with a volume ratio of n-octane to toluene of 1:0.2 to 1:10 to obtain a solution A with a concentration of 10 mg/mL to 100 mg/mL. The quantum dots were dissolved in the solution A with a mass ratio of quantum dot:ligand molecule of 1:0.2 to 1:10 for ligand exchange. The ligand exchange was carried out at room temperature for 20 minutes to 1 hour. The reaction solution was precipitated with ethanol and centrifuged, and then the supernatant was removed. The residue was dissolved with octane and was again precipitated using ethyl acetate. After centrifugation, the supernatant was removed. The residue was dissolved with octane, and the obtained solution was again precipitated with ethyl acetate. Finally, the precipitate was dissolved with octane to form a quantum dot solution with a concentration of from 2 mg/mL to 10 mg/mL.

Figure 8:
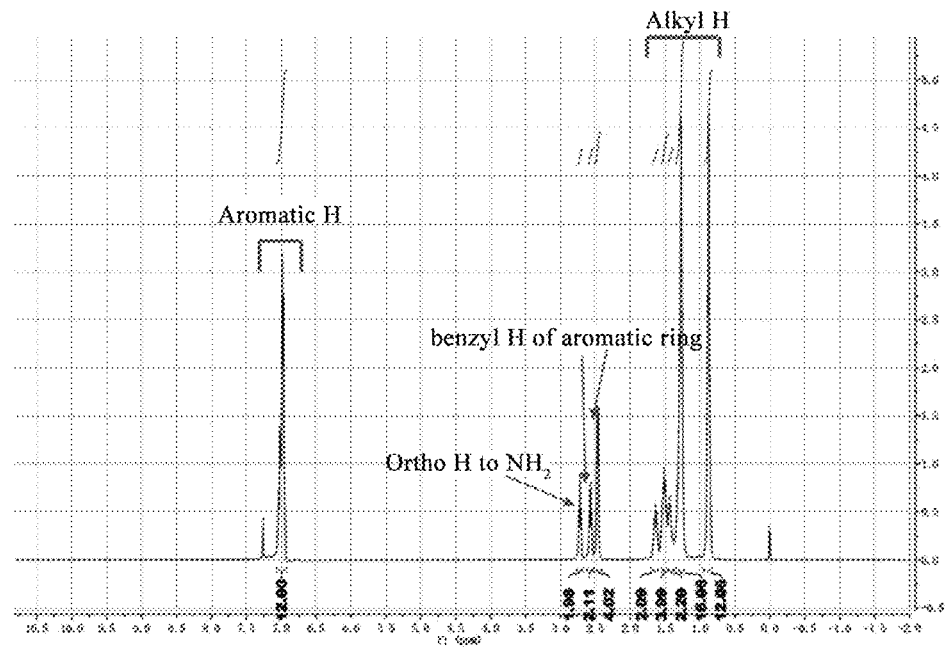
FIG. 8 is a nuclear magnetic hydrogen spectrum of ligand molecule B provided by an embodiment of the present disclosure.

For example, FIG. 8 is $^1$H NMR of ligand molecule B provided by an embodiment of the present disclosure. As shown in FIG. 8, the hydrogen of the aryl group, the hydrogen of the ortho position of the amino group, the hydrogen of the aromatic ring benzyl group, and the hydrogen of the alkyl group are all reflected. The hydrogens in the NMR spectrum in FIG. 8 can correspond to the hydrogens in the structural formula of the ligand molecule B one by one. Combined with the molecular ion peak value in high-resolution mass spectrometry, it can be confirmed that the ligand molecule B is synthesized.

Figure 9:
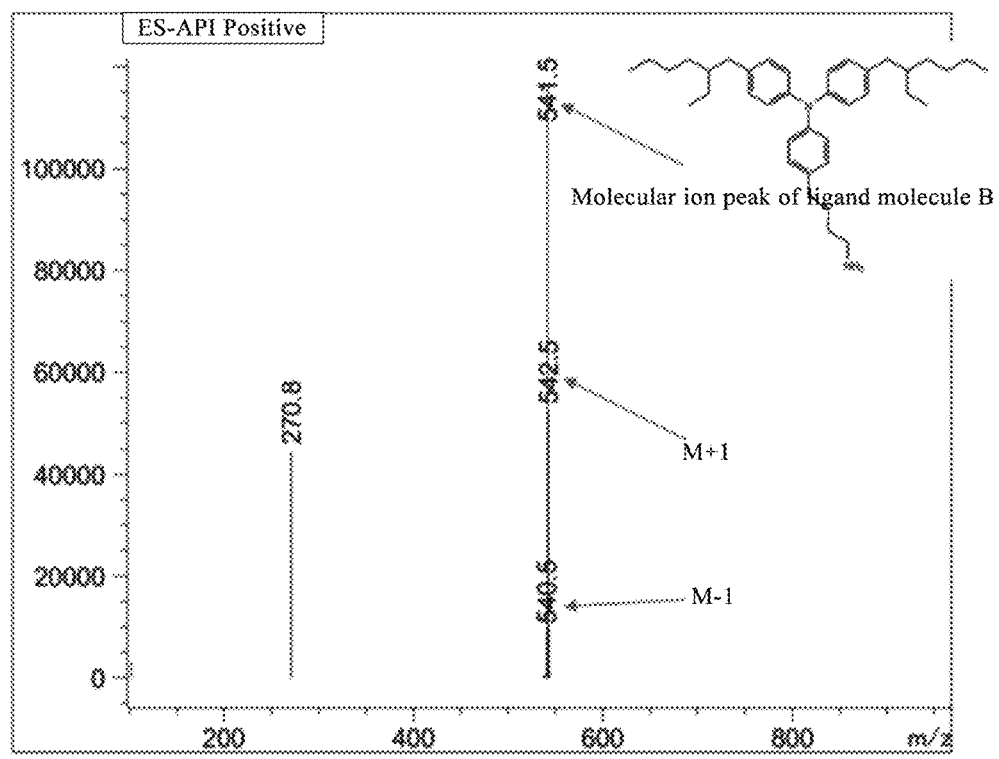
FIG. 9 is a high-resolution mass spectrogram of ligand molecule B provided by an embodiment of the present disclosure.

For example, FIG. 9 is a high-resolution mass spectrum of ligand molecule B provided by an embodiment of the present disclosure. As shown in FIG. 9, the three substitutions at the X group, the Y group and the Z group are all reflected.

Figure 10:
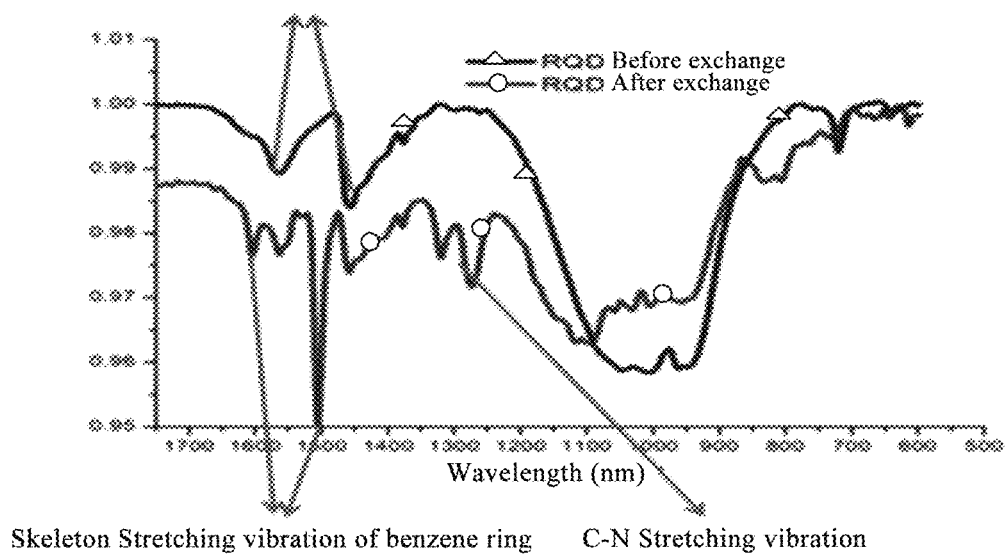
FIG. 10 shows an infrared spectrum diagram before and after quantum dot ligand exchange using ligand molecule B provided by an embodiment of the present disclosure.

For example, FIG. 10 is an infrared spectrum before and after ligand exchange provided by an embodiment of the present disclosure. For example, infrared spectrum characterizes the changes in functional groups of ligands on the surface of quantum dots. As shown in FIG. 10, after the exchange is completed, the stretching vibration peak of the carbon-carbon double bond of the aliphatic chain disappears, and a characteristic peak of the skeleton stretching vibration of the benzene ring and the stretching vibration peak of the carbon-nitrogen bond newly appear. The appearance of the characteristic peak of aromatic ring and the stretching vibration peak of carbon-nitrogen bond confirmed the success of the ligand exchange.

The second example: Preparation of a quantum dot material with triphenylamine-based ligand molecule B.

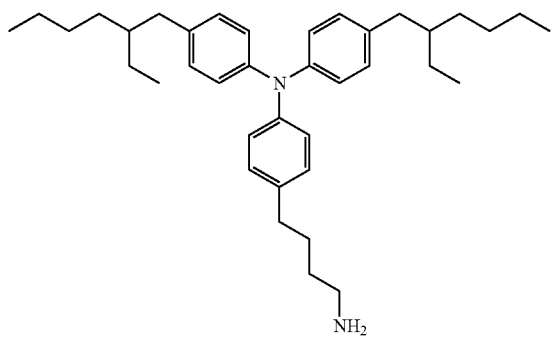 [SMILES: CCCCC(CC)Cc1ccc(N(c2ccc(CCCCN)cc2)c2ccc(CC(CC)CCCC)cc2)cc1]

The synthesized triphenylamine-based ligand molecule B was dissolved in xylene to form a solution. The quantum dots were dissolved in the solution with a mass ratio of quantum dot:ligand molecule B of 1:3 for ligand exchange. The ligand exchange was carried out at room temperature for half an hour. The reaction solution was precipitated with ethanol and centrifuged, and then the supernatant was removed. The residue was dissolved with xylene and was again precipitated using ethyl acetate. After centrifugation, the supernatant was removed. The residue was dissolved with xylene, and the obtained solution was again precipitated with ethyl acetate. Finally, the precipitate was dissolved with xylene to form a quantum dot solution with a concentration of 40 mg/mL.

The third example: Preparation of quantum dot materials with triphenylamine-based ligand molecule C.

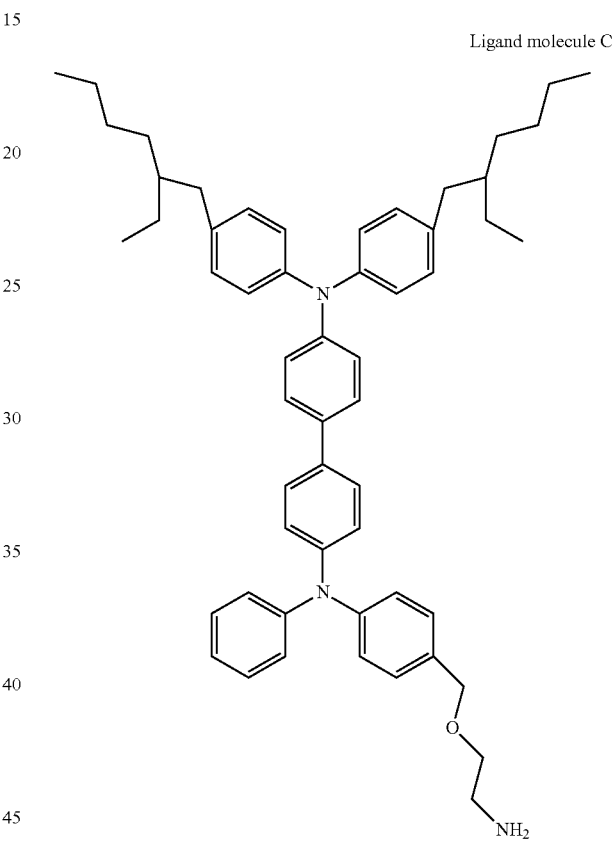

Ligand molecule C

The synthesized triphenylamine-based ligand molecule C was dissolved in xylene to form a solution. The quantum dots were dissolved in the solution with a mass ratio of quantum dot:ligand molecule C of 1:3 for ligand exchange The ligand exchange was carried out at room temperature for half an hour. The reaction solution was precipitated with ethanol and centrifuged, and then the supernatant was removed. The residue was dissolved with xylene, and was again precipitated using ethyl acetate. After centrifugation, the supernatant was removed. The residue was dissolved with xylene, and the obtained solution was again precipitated with ethyl acetate. Finally, the precipitation was dissolved with xylene to form of a quantum dot solution with a concentration of 40 mg/mL.

For example, the stability of quantum dots is characterized as follows: by measuring the change in fluorescence intensity of a quantum dot material in a series of buffer solutions at different pH over time, the stability change of the quantum dot material under different pH environments can be obtained.

At least one embodiment of the present disclosure further provides a quantum dot light emitting device including a quantum dot light emitting layer, wherein the material of the quantum dot light emitting layer include the quantum dot ligand described in any one of the above embodiments and a quantum dot.

For example, the quantum dot light emitting device provided by at least one embodiment of the present disclosure further includes: a hole injection layer, a hole transport layer, an electron injection layer, and an electron transport layer.

Figure 11:
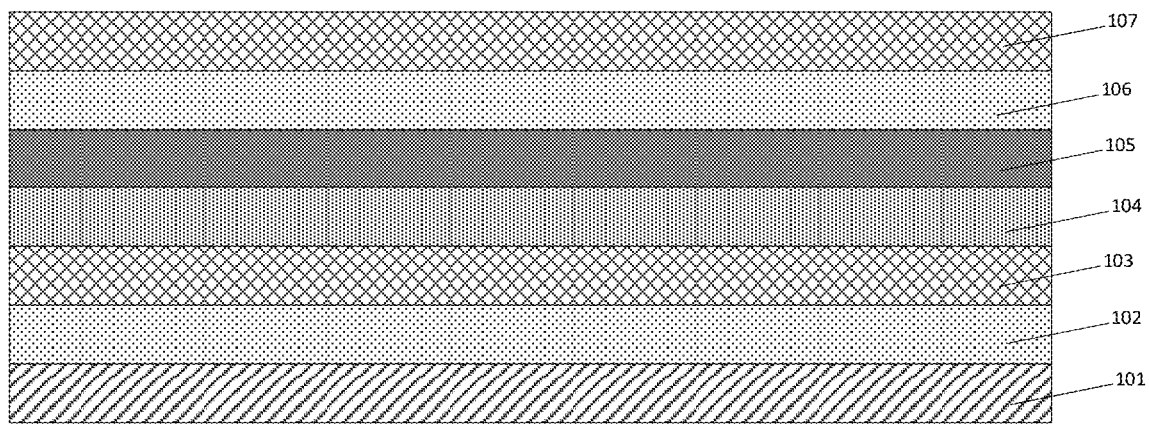
FIG. 11 is a schematic diagram of a cross-sectional structure of a quantum dot light emitting device provided by an embodiment of the present disclosure.

For example, FIG. 11 is a schematic diagram of a cross-sectional structure of a quantum dot light emitting device provided by an embodiment of the present disclosure. As shown in FIG. 11, the quantum dot light emitting device includes a first electrode 101, a hole injection layer 102, a hole transport layer 103, a quantum dot light emitting layer 104, an electron transport layer 105, an electron injection layer 106, and a second electrode 107.

For the preparation methods and materials of the above layers, please refer to the conventional design, which will not be described here.

For example, when a quantum dot material completely exchanged with a new ligand was used in a quantum dot light emitting device, a red light QLED device was prepared according to the illustrated structure, and related tests were performed.

For example, the energy level of the material of the quantum dot light emitting layer can be obtained by AZ-2 X-ray photoelectron spectroscopy. The specific test process is bombarding a quantum dot membrane by X-rays to make electrons escape from the quantum dot membrane, and then calculating by the formula HOMO=hv(21.22 ev)−(EVB-E (cutoff)). Table 1 below is a table comparing the HOMO energy levels of a CdSe/ZnS quantum dot membrane before and after the exchange with ligand molecule A. Commercial RQD is purchased from Suzhou Xingshuo Nanotechnology Co., Ltd. It is quantum dot with CdSe/ZnS core-shell structure, which has oleic acid ligand on the surface before ligand exchange of the quantum dot.

TABLE 1

| Materials of quantum dot light emitting layer | Energy levels |
| --- | --- |
| Purchased RQD | HOMO −5.65 eV |
| Ligand molecule A | HOMO −5.17 eV |
| Ligand molecule A-RQD | HOMO −5.35 eV |

As shown in Table 1 above, the energy level of the ligand molecule A-RQD is located between the purchased RQD and the ligand molecule A, so that the HOMO energy level of the quantum dot material after ligand exchange can be adjusted.

Using an IVL optical measuring instrument and a measuring voltage from 3V to 8V, the current efficiency and EQE were calculated by measuring the brightness and current. Table 2 below shows the results of performance characterization of a quantum dot light emitting device before and after the ligand exchange of CdSe/ZnS red light quantum dots.

TABLE 2

| | | Test results of device | |
| --- | --- | --- | --- |
| | | Average | Maximum |
| Ligand molecule A-RQLED | Current efficiency (cd/A) | 11.6 | 13.8 |
| | EQE (%) | 10.3 | 10.7 |
| Purchased quantum dot-QLED | Current efficiency (cd/A) | 1.7 | 1.85 |
| | EQE (%) | 1.5 | 1.6 |

As shown in Table 2 above, the current efficiency (cd/A) and EQE (%) of the ligand molecule A-RQLED are significantly higher than those of the purchased quantum dot-QLED.

Table 3 below is a table comparing the HOMO energy levels of an indium phosphide quantum dot membrane before and after the exchange with the ligand molecule B. The purchased RQD in Table 3 below is indium phosphide quantum dot, which is purchased from Suzhou Xingshuo Nanotechnology Co., Ltd., and has oleic acid ligand on the surface before the ligand exchange of the quantum dot.

TABLE 3

| Materials of quantum dot light emitting layer | Energy levels |
| --- | --- |
| Purchased RQD | HOMO −5.65 eV |
| Ligand molecule B | HOMO −5.22 eV |
| Ligand molecule B-RQD | HOMO −5.45 eV |

As shown in Table 3 above, the energy level of the ligand molecule B-RQD is located between the purchased RQD and the ligand molecule B, so that the HOMO energy level of the indium phosphide quantum dot material after the ligand exchange can be adjusted.

Embodiments disclosed herein provide a quantum dot ligand, a quantum dot material, and a quantum dot light emitting device, which have at least one of the following beneficial effects: when a small molecule or polymer based on triphenylamine is used as a quantum dot ligand, the energy level of the surface of the quantum dot can be adjusted; the injection balance of electrons and holes in a quantum dot light emitting device can be adjusted to increase the efficiency of the quantum dot light emitting device.

The following points need to be explained:

(1) The drawings of the embodiments disclosed herein relate only to the structures related to the embodiments disclosed herein, and other structures may refer to the general design;

(2) For the sake of clarity, in the drawings used to describe the embodiments disclosed herein, the thickness of layers or regions is enlarged or reduced, that is, these drawings are not drawn according to actual scale;

(3) In the case of no conflict, the embodiments disclosed herein and the features in the embodiments can be combined with each other to obtain new embodiments.

The above are only specific embodiments of the present invention, but the protection scope of the present invention is not limited thereto. The protection scope of the present invention shall be defined by the claims.

What is claimed is:

1. A quantum dot ligand of general formula (I),

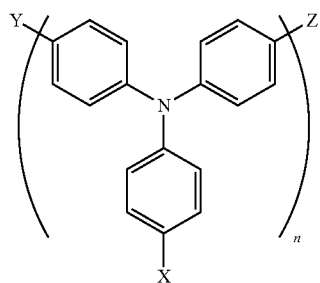

(I)

wherein
n is 1, 2, 3 or 4;
two of X, Y and Z are G1 group and G2 group, respectively, and the remaining one is selected from the group consisting of G1 group, G2 group and hydrogen; wherein
  the G1 group, for each occurrence, is independently selected from —$(CH_2)_m$-L-$(CH_2)_n$—$R^1$, wherein $R^1$ is a coordination group, m is 1 to 6, n is 0 to 6, and L is a divalent group; and
  the G2 group, for each occurrence, is independently selected from a $C_{4-20}$ alkyl having a carbon chain with more than 4 carbon atoms.

2. The quantum dot ligand according to claim 1, having a molecular structure of

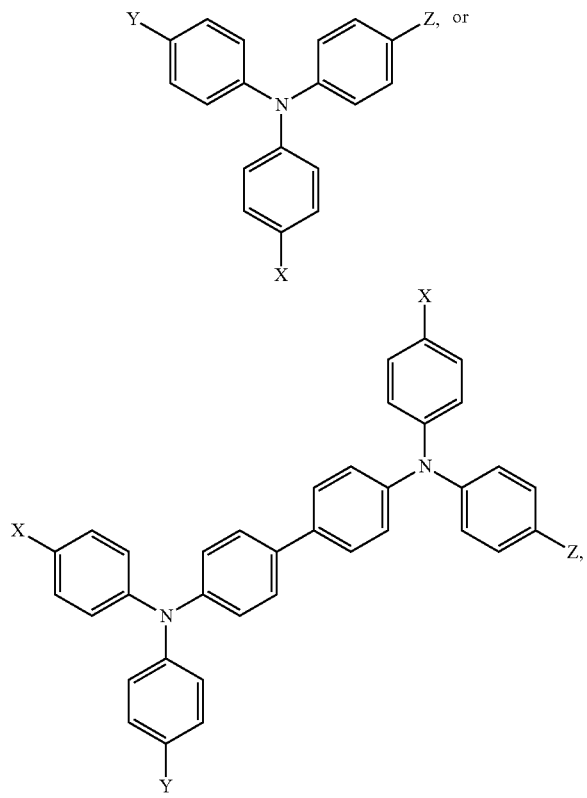

wherein X, Y, and Z are as defined in claim 1.

3. The quantum dot ligand according to claim 1, wherein G1 is —$(CH_2)_m$-L-$(CH_2)_n$-$R^1$, wherein
L is selected from the group consisting of O, NH, S, a linear $C_1$-$C_6$-alkylene, a branched $C_3$-$C_6$-alkylene, a $C_3$-$C_6$-cycloalkylene and a $C_6$-$C_{12}$ arylene, and L is optionally substituted with a substituent(s) selected from the group consisting of oxo, halogen, CN, mercapto, hydroxy, $C_{1-6}$ alkyl, and $C_3$-$C_6$-cycloalkyl;
$R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group;
m is an integer of 1 to 6; and
n is an integer of 0 to 6.

4. The quantum dot ligand according to claim 1, wherein G1 is —$CH_2$-L-$(CH_2)_2$—$R^1$; $R^1$ is $NH_2$; and L is O, NH, S, or $CH_2$.

5. The quantum dot ligand according claim 1, wherein G1 is —$R^1$, and $R^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

6. The quantum dot ligand according to claim 1, wherein the G2 group is a linear alkyl with 4 to 8 carbon atoms; or the G2 group is a branched alkyl with 6 to 12 carbon atoms in the main chain and 2 to 6 carbon atoms in the branch chain.

7. The quantum dot ligand according to claim 1, having a molecular structure of:

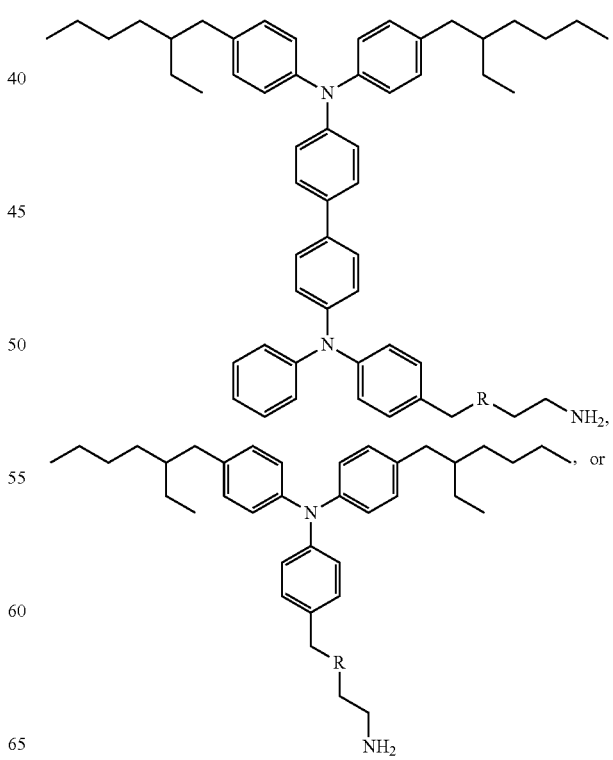

-continued

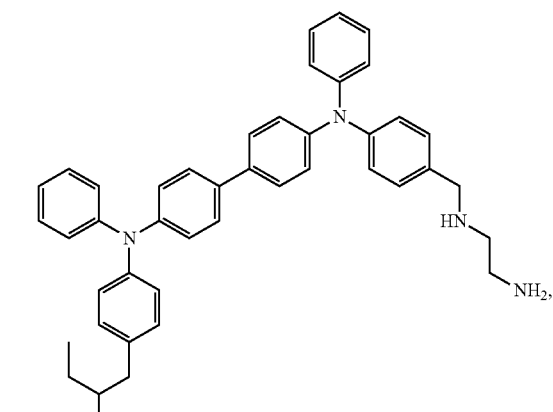

wherein R is O, NH, S or CH$_2$.

8. A quantum dot material comprising:
a quantum dot, and
the quantum dot ligand according to claim 1.

9. The quantum dot material according to claim 8, wherein the quantum dot is selected from the group consisting of CdS, CdSe, CdTe, ZnSe, InP, PbS, CsPbCl$_3$, CsPbBr$_3$, CsPhI$_3$, CdS/ZnS, CdSe/ZnS, ZnSe, InP/ZnS, PbS/ZnS, CsPbCl$_3$/ZnS, CsPbBr$_3$/ZnS and CsPhI$_3$/ZnS.

10. A quantum dot light emitting device comprising a quantum dot light emitting layer, wherein the quantum dot light emitting layer comprises the quantum dot material of claim 8.

11. The quantum dot light emitting device according to claim 10, further comprising: a hole injection layer, a hole transport layer, an electron injection layer, and an electron transport layer.

12. The quantum dot material according to claim 8, wherein the quantum dot ligand has a molecular structure of

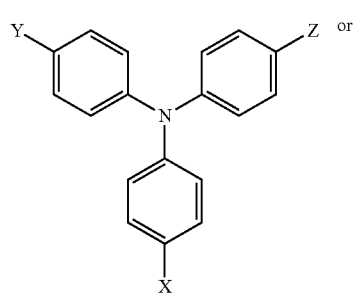 or

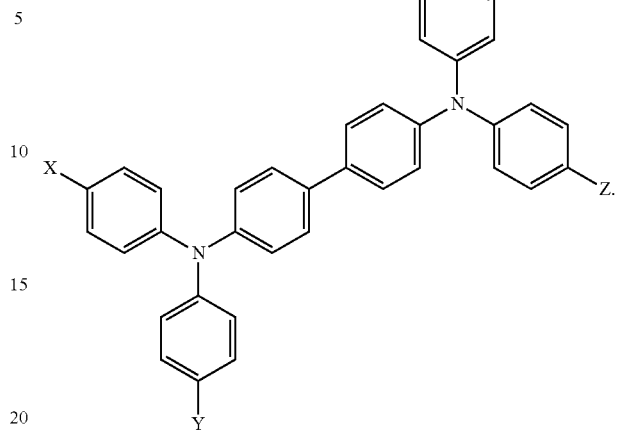

wherein
two of X, Y and Z are G1 group and G2 group, respectively, and the remaining one is selected from the group consisting of G1 group, G2 group and hydrogen; wherein
  the G1 group, for each occurrence, is independently selected from —(CH$_2$)$_m$-L-(CH$_2$)$_n$—R$^1$, wherein R$^1$ is a coordination group, m is 1 to 6, n is 0 to 6, and L is a divalent group; and
  the G2 group, for each occurrence, is independently selected from a C$_{4-20}$ alkyl having a carbon chain with more than 4 carbon atoms.

13. The quantum dot material according to claim 12, wherein G1 is —(CH$_2$)$_m$-L-(CH$_2$)$_n$—R$^1$, wherein
L is selected from the group consisting of O, NH, S, a linear C$_1$-C$_6$-alkylene, a branched C$_3$-C$_6$-alkylene, a C$_3$-C$_6$-cycloalkylene and a C$_6$-C$_{12}$ arylene, and L is optionally substituted with a substituent(s) selected from the group consisting of oxo, halogen, CN, mercapto, hydroxy, C$_{1-6}$ alkyl, and C$_3$-C$_6$-cycloalkyl;
R$^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group;
m is an integer of 1 to 6; and
n is an integer of 0 to 6.

14. The quantum dot material according to claim 12, wherein G1 is -CH2-L-(CH$_2$)$_2$—R$^1$; R$^1$ is NH$_2$; and L is O, NH, S, or CH$_2$.

15. The quantum dot material according to claim 12, wherein G1 is —R$^1$, and R$^1$ is selected from the group consisting of a mercapto group, a hydroxyl group, an amine group, an amino group, a carboxyl group, a phosphine group, a phosphine oxide group, a phosphoric acid group, a phosphoric acid ester group, and a sulfonic acid group.

16. The quantum dot material according to claim 12, wherein the G2 group is a linear alkyl with 4 to 8 carbon atoms; or the G2 group is a branched alkyl with 6 to 12 carbon atoms in the main chain and 2 to 6 carbon atoms in the branch chain.

17. The quantum dot material according to claim 12, wherein the quantum dot ligand has a molecular structure of:

37
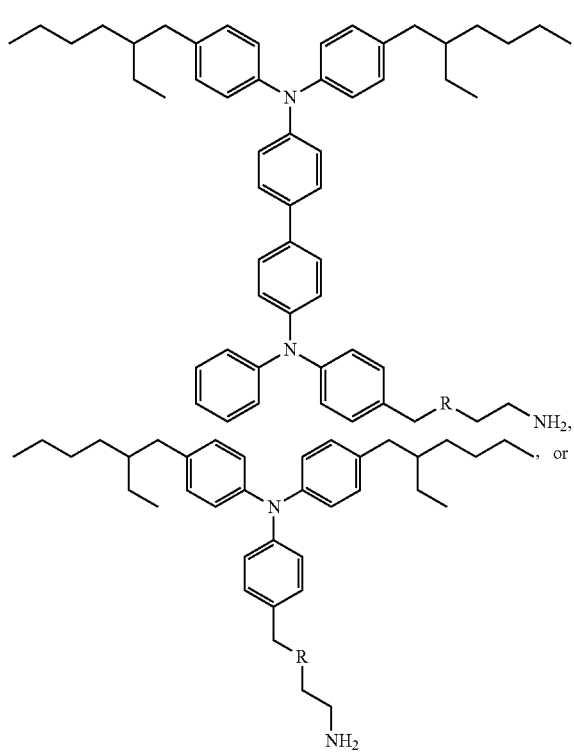
38
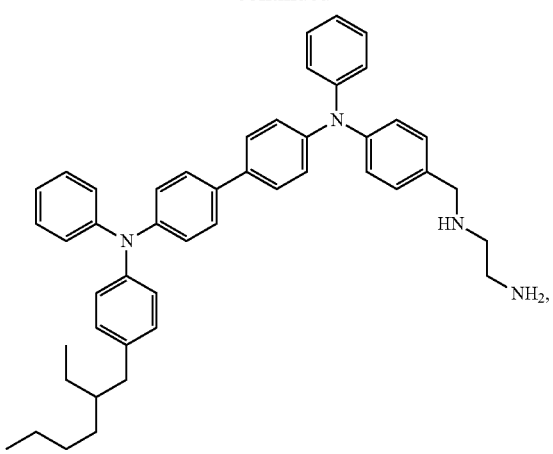
wherein R is O, NH, S or CH$_2$.
* * * * *